United States Patent
Iseberg et al.

(10) Patent No.: US 10,624,562 B2
(45) Date of Patent: Apr. 21, 2020

(54) HEARING TESTING PROBE APPARATUS WITH DIGITAL INTERFACE

(71) Applicant: Etymotic Research, Inc., Elk Grove Village, IL (US)

(72) Inventors: Steve Iseberg, Crystal Lake, IL (US); Mead C. Killion, Elk Grove Village, IL (US); Jonathan Siegel, Skokie, IL (US); Sumitrajit Dhar, Skokie, IL (US); Viorel Drambarean, Lincolnwood, IL (US); Dan Mapes-Riordan, Evanston, IL (US); Steve Viranyi, Palatine, IL (US)

(73) Assignee: ETYMOTIC RESEARCH, INC., Elk Grove Village, IL (US)

( * ) Notice: Subject to any disclaimer, the term of this patent is extended or adjusted under 35 U.S.C. 154(b) by 566 days.

(21) Appl. No.: 14/868,814

(22) Filed: Sep. 29, 2015

(65) Prior Publication Data

US 2016/0113554 A1   Apr. 28, 2016

Related U.S. Application Data

(63) Continuation of application No. 13/357,184, filed on Jan. 24, 2012, now Pat. No. 9,155,494.

(60) Provisional application No. 61/435,620, filed on Jan. 24, 2011.

(51) Int. Cl.
*A61B 5/12* (2006.01)
*A61B 5/00* (2006.01)

(52) U.S. Cl.
CPC ............ *A61B 5/121* (2013.01); *A61B 5/6817* (2013.01)

(58) Field of Classification Search
CPC ............ H04R 25/70; A61B 5/121; A61B 5/12
USPC ......................................................... 600/559
See application file for complete search history.

(56) References Cited

U.S. PATENT DOCUMENTS

| | | | |
|---|---|---|---|
| 3,882,848 A | | 5/1975 | Klar et al. |
| 4,014,320 A | | 3/1977 | Richards |
| 4,029,083 A | | 6/1977 | Baylor |
| 5,664,577 A | | 9/1997 | Lonsbury-Martin |
| 5,823,965 A | * | 10/1998 | Rasmussen ............ A61B 5/085 600/462 |
| 5,954,669 A | | 9/1999 | Iseberg |

(Continued)

OTHER PUBLICATIONS

PCT Notification Concerning Transmittal of International Preliminary Report on Patentability, in International Application No. PCT/US2012/022347, dated Aug. 8, 2013 (7 pages).

(Continued)

*Primary Examiner* — Daniel L Cerioni
(74) *Attorney, Agent, or Firm* — McAndrews, Held & Malloy, Ltd.

(57) ABSTRACT

Certain embodiments provide a hearing testing probe apparatus. The hearing testing probe apparatus includes a probe tube detachably coupled at a first end to a probe body and extending through a center hole in an eartip to align proximate a face of the eartip at a second end. The probe tube includes a plurality of stimulus lumens for receiving and carrying stimulus from the first end of the probe tube for output at the second end of the probe tube. The probe tube includes one or more microphone lumens for receiving and carrying one or more measured responses from the second end of the probe tube to one or more microphones at the first end of the probe tube.

22 Claims, 18 Drawing Sheets

(56) References Cited

U.S. PATENT DOCUMENTS

| | | | |
|---|---|---|---|
| 6,048,320 | A | 4/2000 | Brainard, II |
| 6,110,126 | A | 8/2000 | Zoth et al. |
| 6,299,584 | B1 | 10/2001 | Iseberg |
| 6,368,289 | B2 * | 4/2002 | Stone .................. A61B 5/6817 |
| | | | 181/129 |
| 6,702,758 | B2 | 3/2004 | Iseberg |
| 7,976,474 | B2 | 7/2011 | Zoth et al. |
| 2002/0058881 | A1 | 5/2002 | Raviv et al. |
| 2005/0015018 | A1 | 1/2005 | Dolphin |
| 2006/0282009 | A1 | 12/2006 | Oberg |
| 2007/0112279 | A1 | 5/2007 | Iseberg et al. |
| 2007/0129719 | A1 * | 6/2007 | Kendale ............. A61B 1/00096 |
| | | | 606/41 |
| 2007/0161924 | A1 | 7/2007 | Dolphin et al. |
| 2008/0194984 | A1 | 8/2008 | Keefe |
| 2009/0321177 | A1 | 12/2009 | McMahon |
| 2011/0305361 | A1 * | 12/2011 | Li .......................... C22C 1/005 |
| | | | 381/380 |

OTHER PUBLICATIONS

PCT Notification of Transmittal of the International Search Report and the Written Opinion of the International Searching Authority, or the Declaration, in International Application No. PCT/US2012/022347, dated May 25, 2012 (11 pages).

\* cited by examiner

FIG. 17
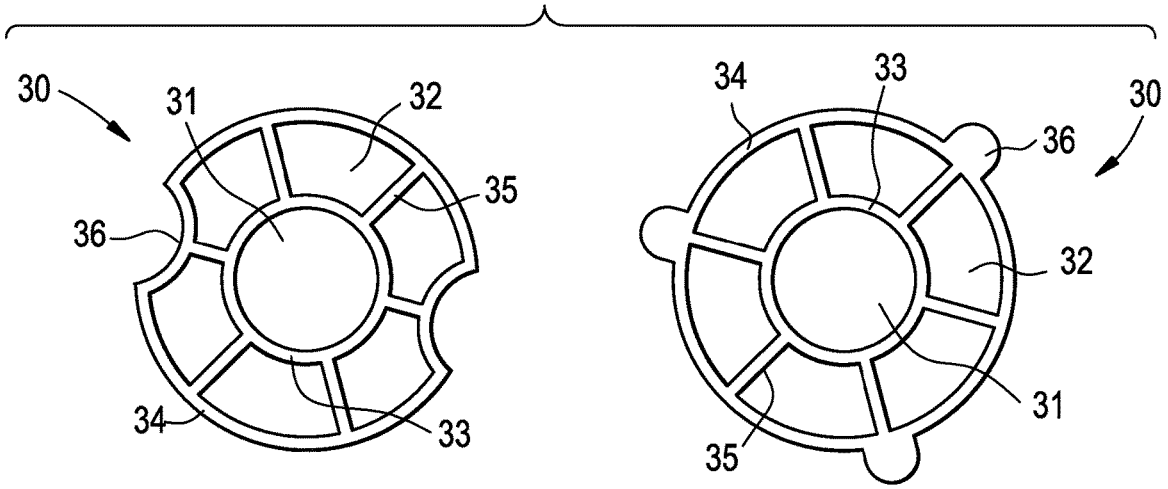
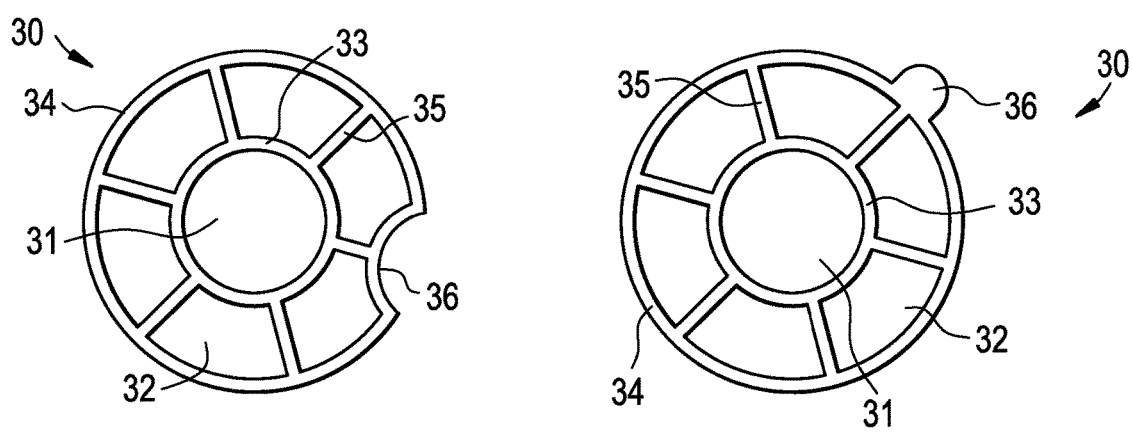
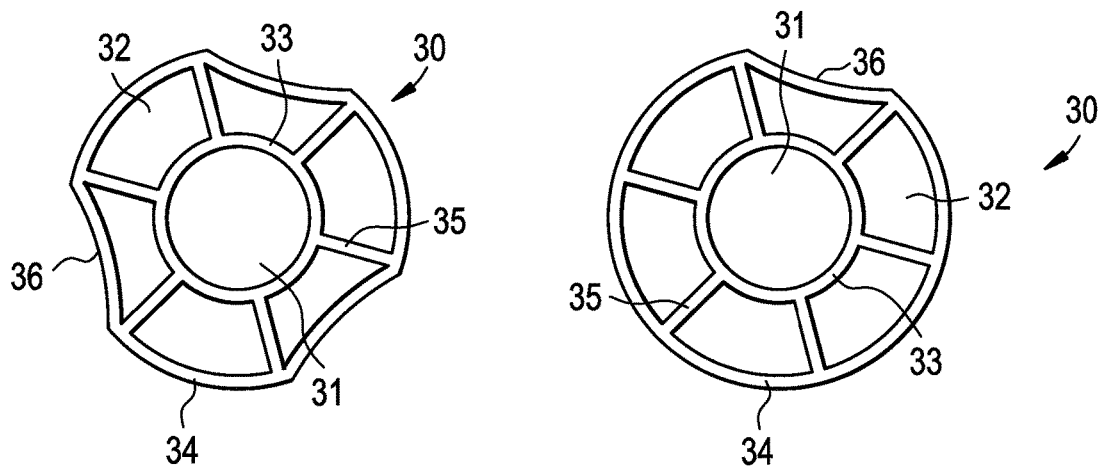

HEARING TESTING PROBE APPARATUS WITH DIGITAL INTERFACE

CROSS-REFERENCE TO RELATED APPLICATIONS/INCORPORATION BY REFERENCE

This application is a continuation of U.S. patent application Ser. No. 13/357,184, entitled "Hearing Testing Probe Apparatus with Digital Interface," filed on Jan. 24, 2012, now U.S. Pat. No. 9,155,494, which makes reference to, claims priority to, and claims benefit from U.S. Provisional Patent Application Ser. No. 61/435,620, entitled "Hearing Testing Probe Apparatus with Digital Interface," filed on Jan. 24, 2011.

The entire contents of each above-mentioned prior-filed application is hereby expressly incorporated herein by reference.

FEDERALLY SPONSORED RESEARCH OR DEVELOPMENT

This invention was made with government support under contract number N00014-10-M-0267 awarded by the Office of Naval Research. The government has certain rights in the invention.

MICROFICHE/COPYRIGHT REFERENCE

[Not Applicable]

BACKGROUND OF THE INVENTION

The present invention relates generally to hearing testing probes placed within ear canals that are coupled to an instrument that monitors the condition within the ears. More specifically, the present invention provides a hearing testing probe with a user-replaceable coupling member for interfacing to an ear canal. The present invention further relates generally to a digital interface for coupling a testing instrument to a hearing testing probe placed within the ear canal. More specifically, the present invention relates to a hearing tester which emits test signals into the ear via a digital interface and through a probe placed within the ear canal, and then uses the response to make a determination of hearing function.

Hearing test devices that monitor the condition within a human ear are known. Such test devices generally require that the person performing the test (the "operator") place a test probe of the device within the ear canal of a test subject. Once the probe is placed properly within the ear canal, the operator activates the device, usually by pressing a button or the like. The device then emits test signals into the subject's ear through the probe in the ear canal. In response to the test signals emitted, the device receives response signals from the ear, likewise through the probe in the ear canal. Such response signals received are then used to determine whether the ear is functioning properly.

Audiological testing for hearing impairment commonly requires an acoustic, air pressure, or vibratory stimulus to be presented to the test subject. Several of the methods for hearing evaluation require the use of a probe to generate and couple the stimulus directly to the subject's ear canal. Examples of hearing tests using these probes include otoacoustic emissions, acoustic immittance, acoustic reflex, reflectance, and, in some cases, auditory brainstem response. For each of these tests, certain characteristics of the stimulations need to be applied accurately in order to provide an accurate evaluation of the results.

In order to provide an accurate evaluation of the results, frequency response, magnitude, distortion, and other characteristics of the stimulus should be presented appropriately and measured accurately. Current calibration methods become less accurate as the frequency of the desired stimulus increases. Calibration errors become increasingly more significant at frequencies beyond 6 kHz and provide for a much reduced degree of certainty and consistency in measurements of hearing function. While it is desirable to perform measurements at higher frequencies, where often the first indications of hearing loss would be present, the ability to perform repeatable and consistent measurements with currently available commercial hearing testing probes is significantly limited.

For many tests, otoacoustic emissions testing in particular, the levels of stimulus applied to the ear canal of the subject is determined by a calibration sequence performed when the probe is placed into the ear canal of the subject. This calibration of the probe response in the subject's ear canal is critical to determining and applying the appropriate stimulus. Assessment and diagnosis of the test responses are based on the levels of the stimulus applied, and thus the accuracy of the assessment is compromised if the applied levels are not accurate.

During hearing testing, a seal to the ear canal is provided by an eartip containing one or more internal sound channels for conducting sound to and from the end of the probe to the ear. FIG. 1 illustrates an exemplary recessed probe design as is known in the art. The accuracy of the calibration with the commonly available hearing test probes is limited by an intentional design feature. The end of the hearing test probe, where the stimulus exits into the ear canal, is recessed from the end of the eartip. This recess, usually two to three millimeters in length, provides a place for contamination (e.g., cerumen or other biological material) to collect without entering the body of the probe where cleaning or extraction of the contamination would be difficult and can compromise the performance of the probe.

Referring to the exemplary recessed probe design illustrated in FIG. 1, the recessed probe end provides a buffer zone that often contains any contamination and reduces the occurrence of infiltration into the probe body. However, the recessed tip design is not desirable for performing hearing testing at high frequencies because of known errors in performing calibration at high frequencies associated with recessed probe tips.

Evidence of the difficulty in managing contamination in hearing test probes can be seen in recent probe designs where the ear canal end of the probe is made to be user replaceable in the event that contamination gets beyond the recess at the front of the eartip and enters the body of the probe. This solution can provide a more convenient means of contamination removal than many of the cleaning and disassembly procedures used in older designs. However, the cost of the replacement component can be significant even though it is only likely to require replacement after the testing of numerous subjects. This problem would be significantly exacerbated if the probe end is designed to exit flush with, or extend slightly beyond, the end of the eartip.

FIG. 2 illustrates an exemplary replaceable probe tip design as is known in the art. Existing replaceable probe tip designs commonly use a recessed tip design to minimize the occurrence of contamination. As noted above, the recessed tip design is not desirable for performing hearing testing at high frequencies because of known errors in performing calibration at high frequencies associated with recessed probe tips. Additionally, existing replacement probe tips are too expensive and cumbersome to replace frequently.

Another limitation in current hearing probe designs is the minimal area available for the stimulus and microphone acoustic channels through the eartip. A three millimeter outer diameter limitation is the industry standard such that the eartips are small enough to properly fit and seal to the ear canals of infants and newborns. This minimal cross-sectional area of the stimulus and microphone channels causes limitations in the frequency response of the stimulus sources and increases the impedance of the microphone input which causes an increase in its noise floor. Compounding this limitation is the need for the stimulus channels and the microphone channels maintain separation to their exit at the ear canal. Maximizing the use of the three millimeter diameter allowed provides for an improved frequency response and noise floor.

Additionally, existing hearing test instruments typically communicate test signals to a probe and receive the acoustic response signals from the probe in real-time. As such, these existing hearing test devices have been limited to performing a hearing test on one ear at a time.

Also, existing hearing test instruments have been limited in the manner of communication between the probe and the instrument. Specifically, existing hearing test instruments have communicated with the probe using analog electrical signals over a cable. However, the cables used in existing hearing test instruments have limited cable lengths, requiring the patient and tester to be in close proximity and reducing flexibility in probe placement. The limited cable length is largely due to the need to minimize signal degradation when using analog transmissions for the stimulus and responses. The cable is shielded to minimize interference from outside radio frequency (RF) and electromagnetic interference (EMI).

The construction of this communication cable is complicated by the requirement to eliminate interference between the stimulus channels and the microphone channel. The probe cable adds bulk and weight to the system and may pull on the probe in the ear during testing, making it difficult to keep the required seal and positioning in the ear canal.

Further limitations and disadvantages of conventional and traditional approaches will become apparent to one of skill in the art, through comparison of such systems with some aspects of the present invention as set forth in the remainder of the present application with reference to the drawings.

BRIEF DESCRIPTION OF THE DRAWING(S)

An apparatus and/or method is provided for a hearing testing probe with a user-replaceable coupling member for interfacing to an ear canal, substantially as shown in and/or described in connection with at least one of the figures, as set forth more completely in the claims.

These and other advantages, aspects and novel features of the present invention, as well as details of an illustrated embodiment thereof, will be more fully understood from the following description and drawings.

BRIEF DESCRIPTION OF THE DRAWING(S)

FIG. 17 illustrates cross-sectional views of exemplary embodiments of keyed probe tubes used in accordance with an embodiment of the present technology.

Figure 1:
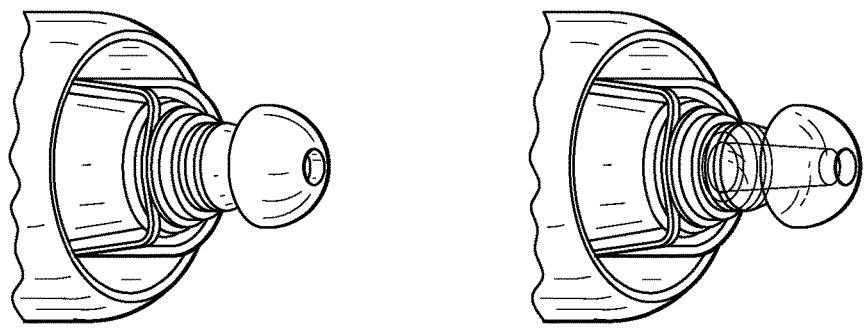
FIG. 1 illustrates an exemplary recessed probe design as is known in the art.

The foregoing summary, as well as the following detailed description of embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION

Embodiments of the present technology provide a hearing testing probe with a user-replaceable coupling member for interfacing to an ear canal. Embodiments of the present technology provide hearing testing probes placed within ear canals that are coupled via a digital interface to an instrument that monitors the condition within the ears.

Figure 3:
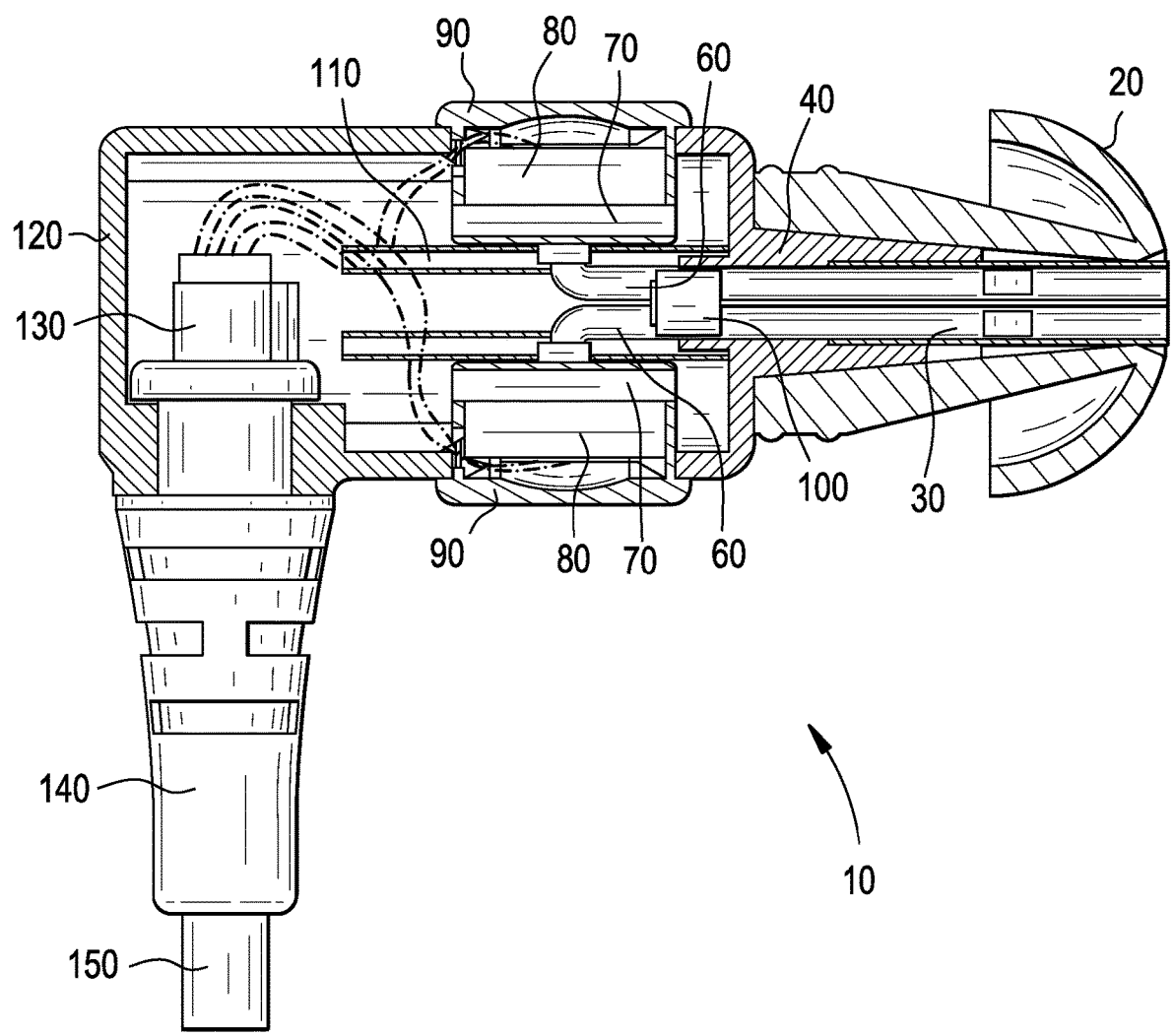
FIG. 3 illustrates a side view in cross-section of an exemplary embodiment of a hearing testing probe used in accordance with an embodiment of the present technology.
Figure 4:
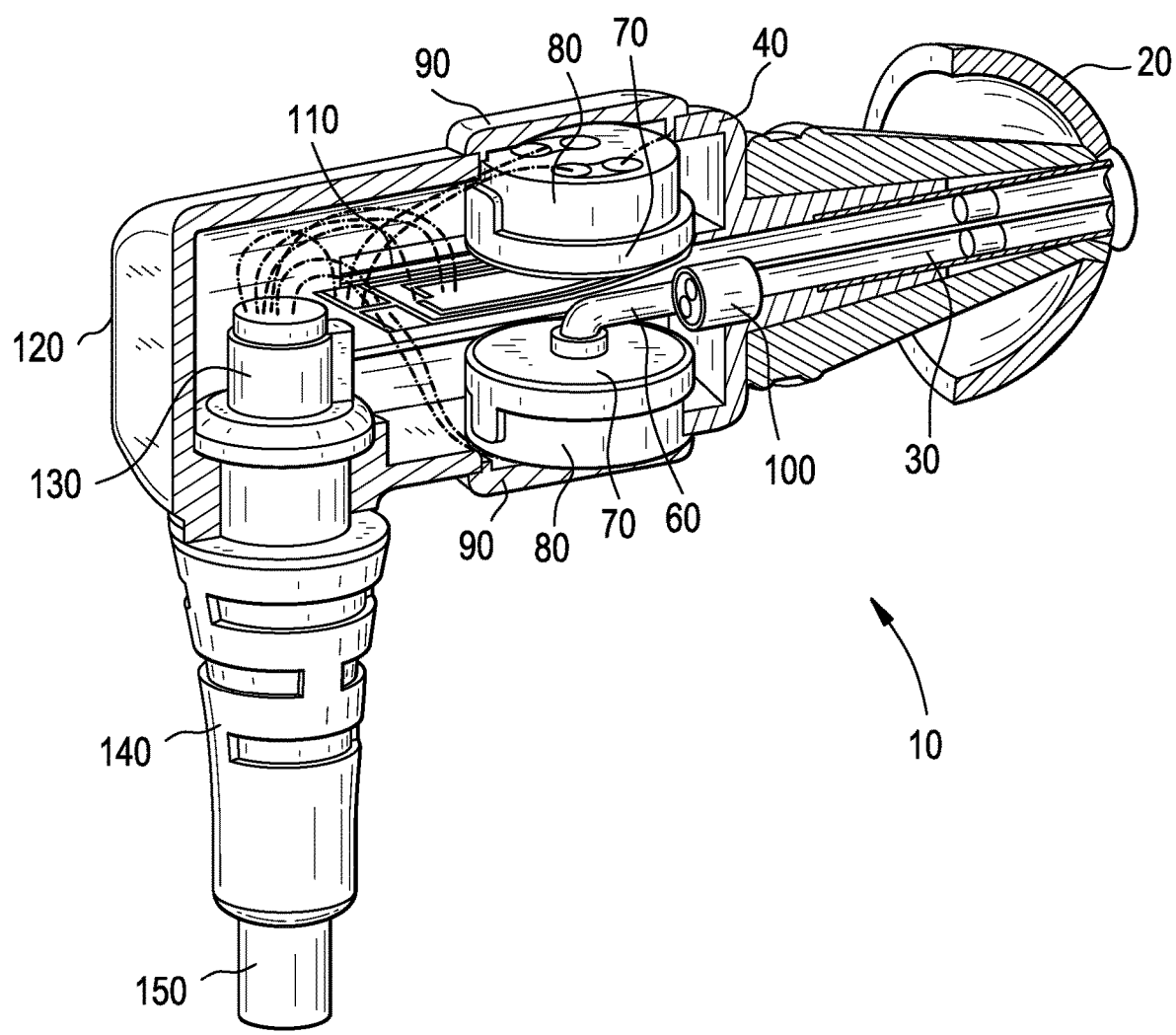
FIG. 4 illustrates another side view in cross-section of an exemplary embodiment of a hearing testing probe used in accordance with an embodiment of the present technology.
Figure 5:
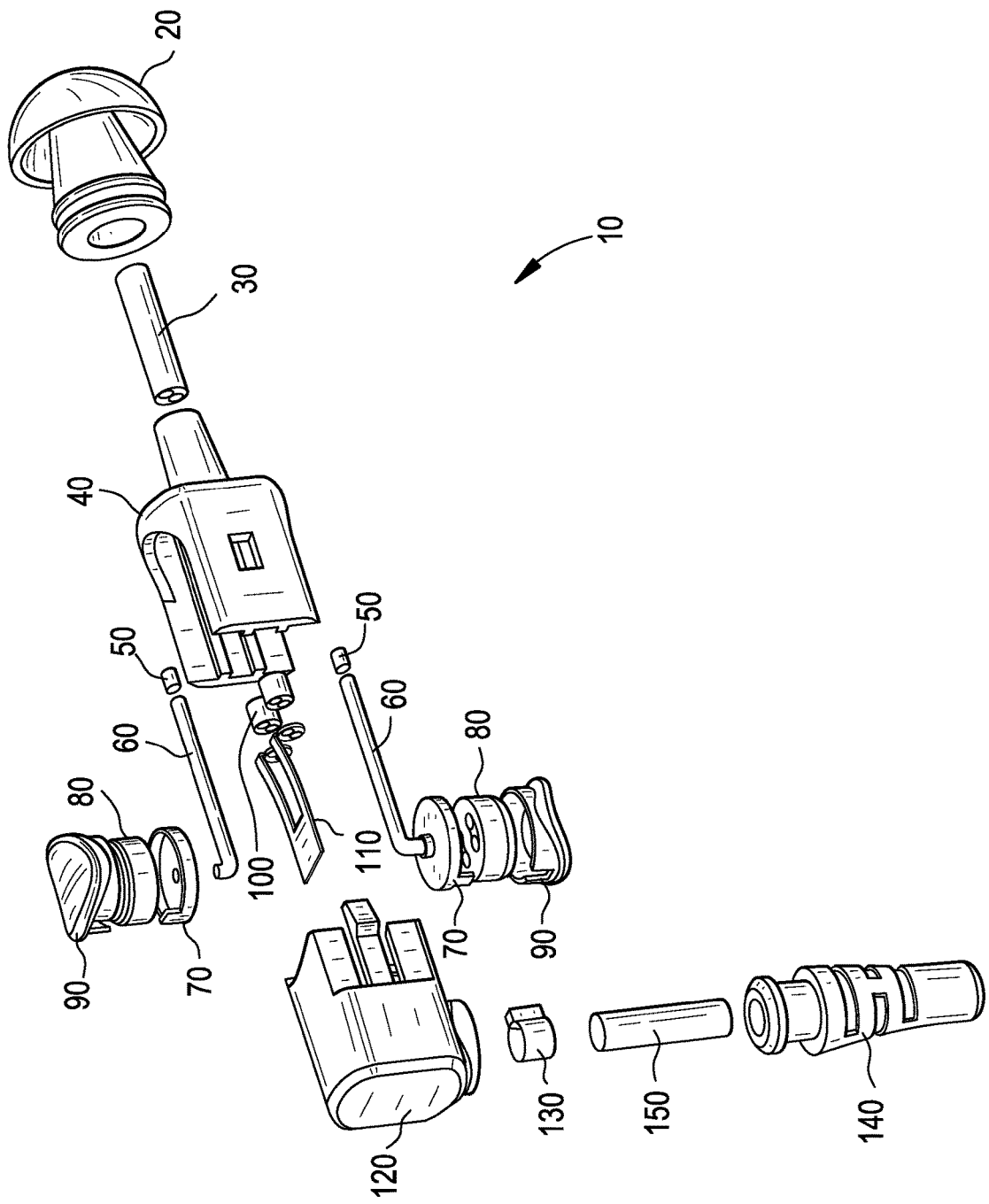
FIG. 5 illustrates an exploded side view of an exemplary embodiment of a hearing testing probe used in accordance with an embodiment of the present technology.
Figure 7:
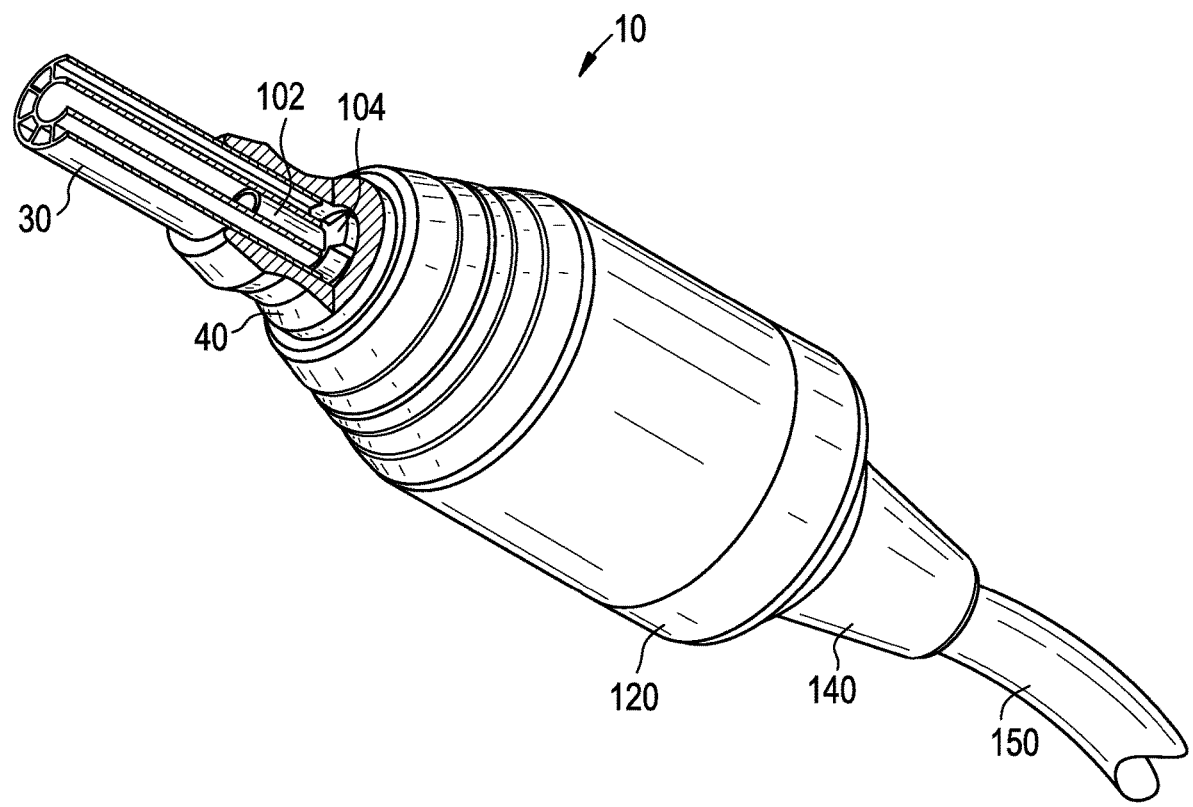
FIG. 7 illustrates a cutaway side view of an exemplary embodiment of a hearing testing probe used in accordance with an embodiment of the present technology.
Figure 8:
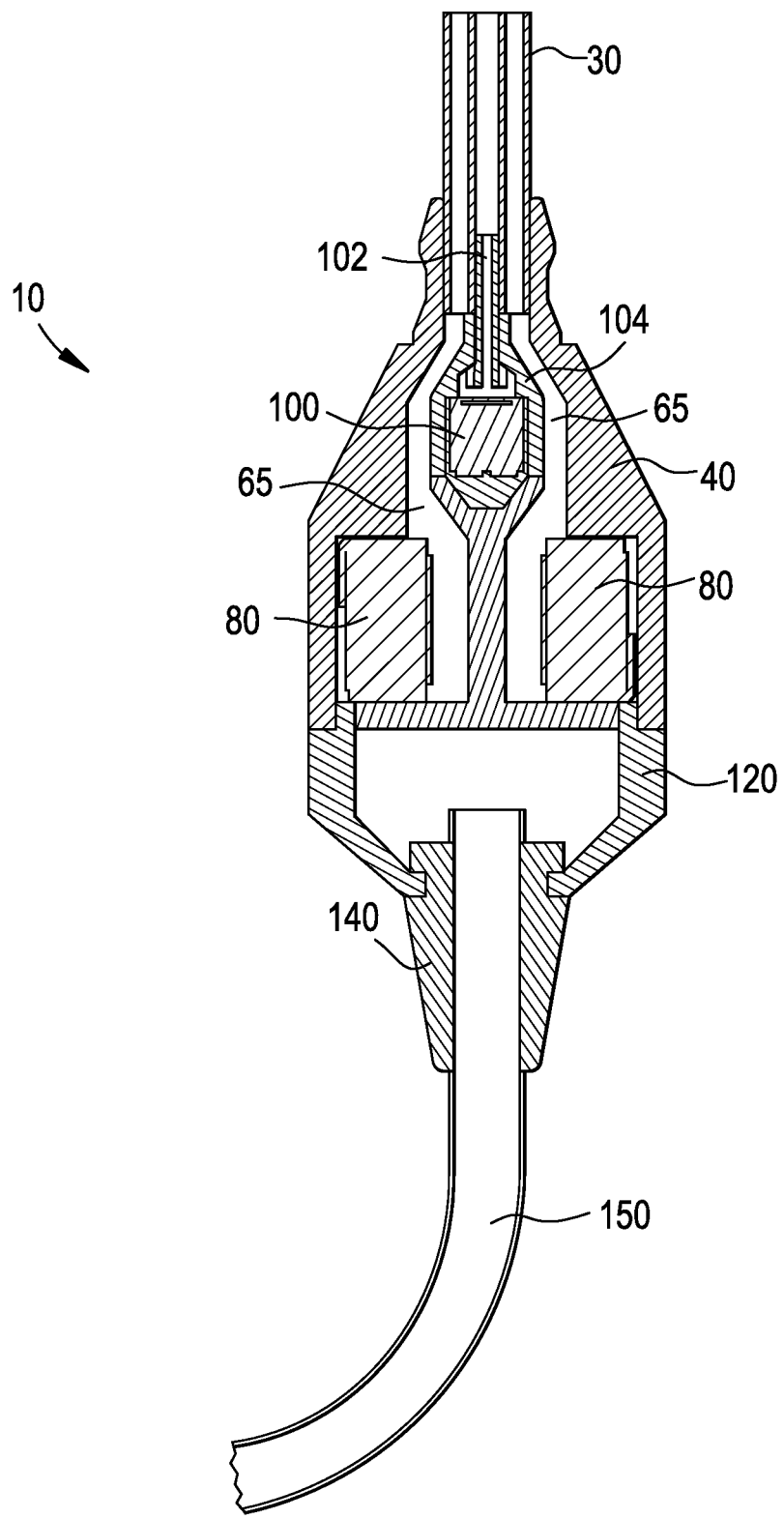
FIG. 8 illustrates a cross-sectional view of an exemplary embodiment of a hearing testing probe used in accordance with an embodiment of the present technology.
Figure 9:
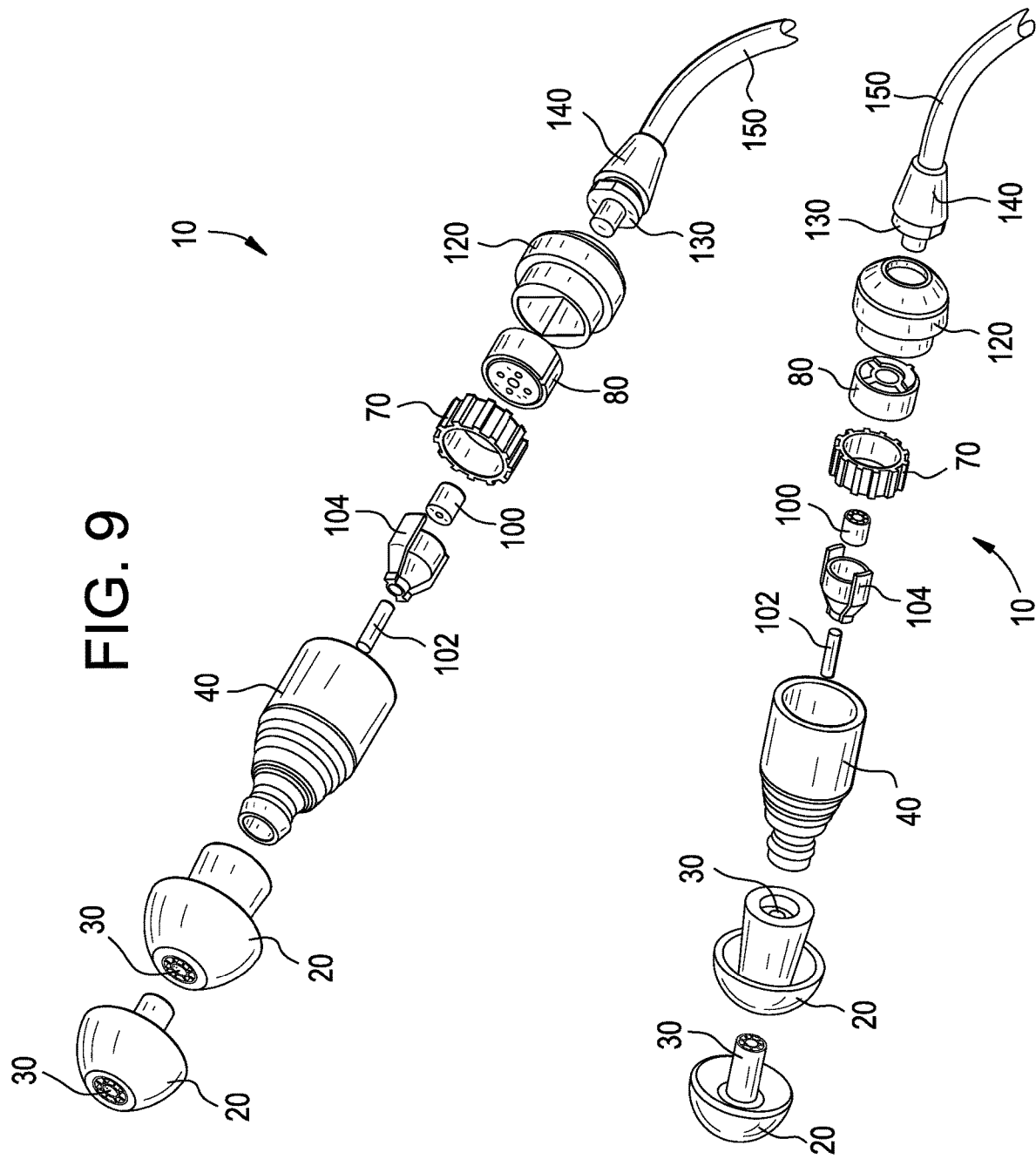
FIG. 9 illustrates exploded side views of an exemplary embodiment of a hearing testing probe used in accordance with an embodiment of the present technology.
Figure 14:
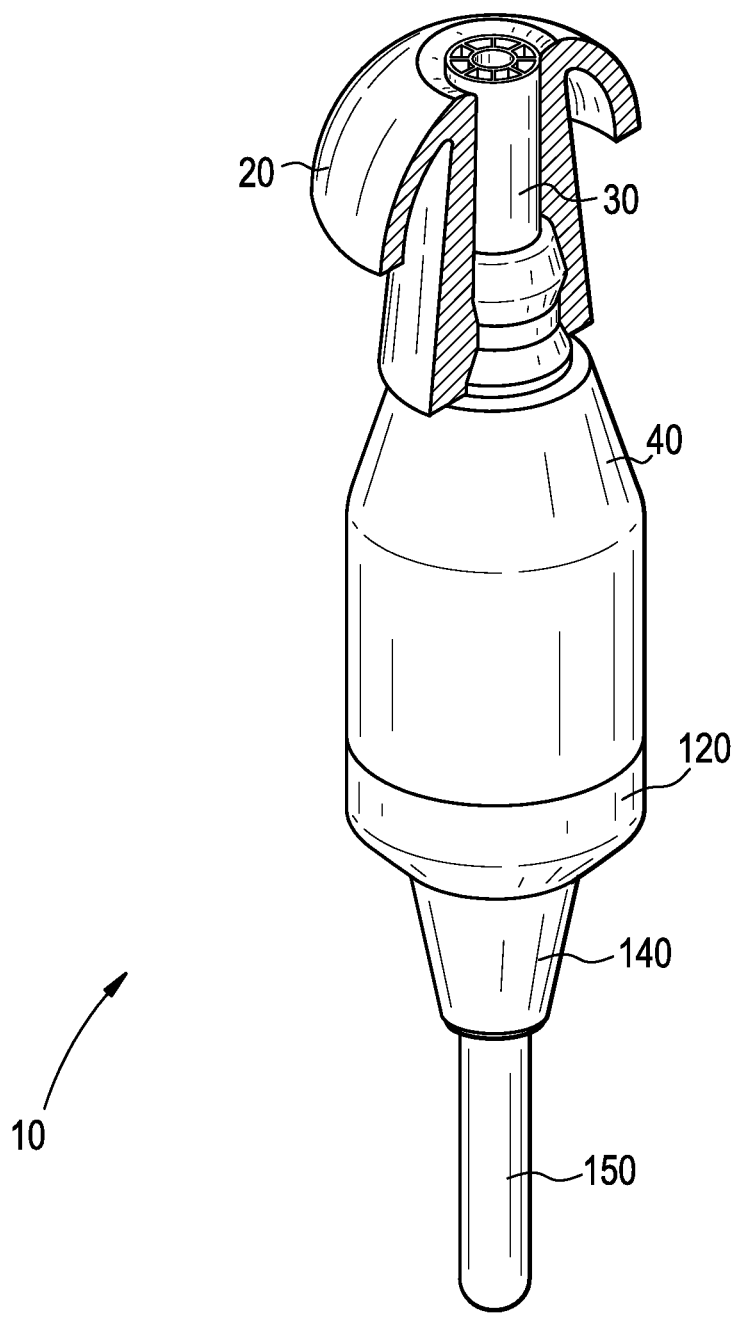
FIG. 14 illustrates a view of an exemplary hearing testing probe and probe tube used with an elastomeric eartip in accordance with an embodiment of the present technology.
Figure 15:
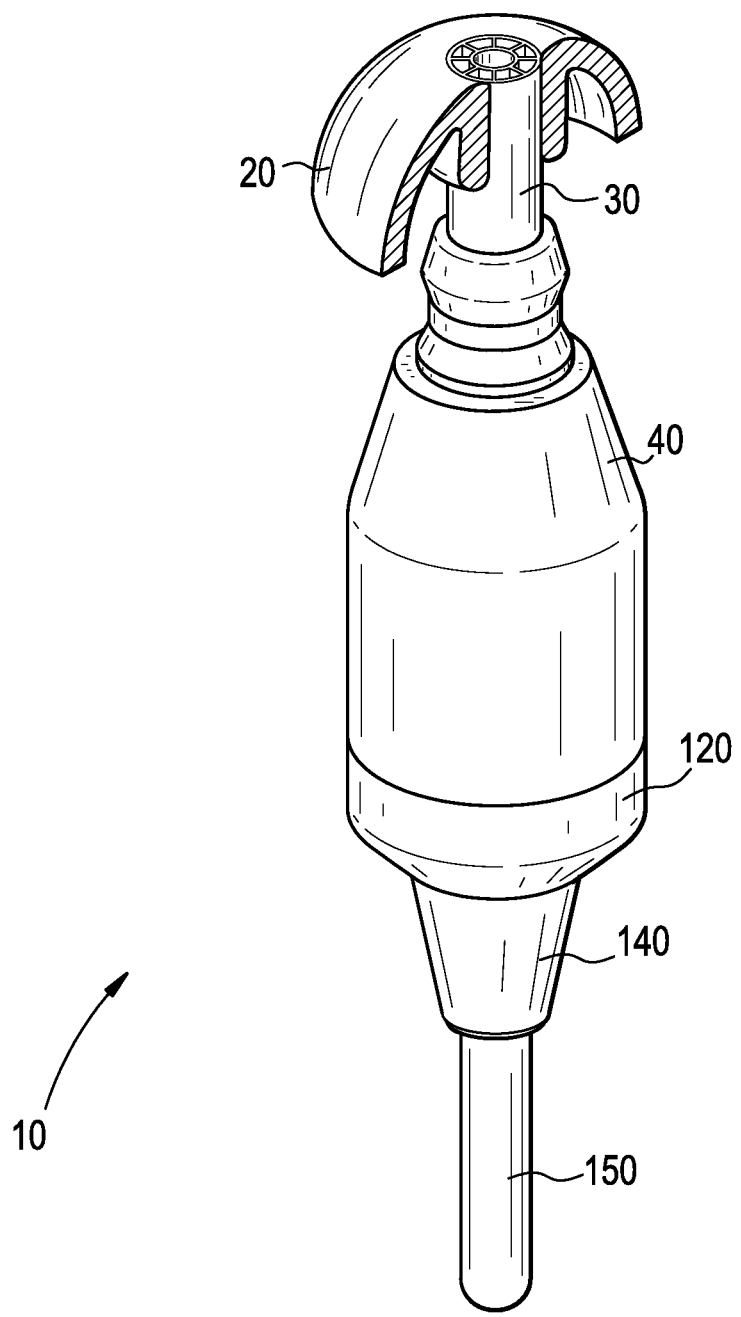
FIG. 15 illustrates a view of an exemplary hearing testing probe and probe tube with an adhered to eartip used in accordance with an embodiment of the present technology.

FIGS. 3-4 and 7-8 illustrate side views in cross-section of exemplary embodiments of the hearing test probe 10 used in accordance with an embodiment of the present technology. FIGS. 5 and 9 illustrate exploded side views of exemplary embodiments of the hearing test probe 10. FIG. 14 illustrates a view of an exemplary hearing testing probe 10 and probe tube 30 used with an elastomeric eartip 20. FIG. 15 illustrates a view of an exemplary hearing testing probe 10 and probe tube 30 with an adhered to eartip 20.

Referring to FIGS. 3-5, 7-9 and 14-15, certain embodiments of a hearing testing probe 10 include a cable 150 for communicating test signals to a probe 10 and receiving the response signals from the probe 10. In an embodiment, cable 150 is inserted in end cap 120 via a grommet 140 for protecting the cable 150 and is secured within the end cap 120 using a cable clamp 130 as illustrated in FIGS. 3-5 and 9, for example. End cap 120 attaches to probe body 40. The end cap 120 and probe body 40 may house various components of the probe 10, including but not limited to drivers 80, driver tubes 60 or stimulus channels 65, sealing and mating surface 104, flex circuit 110, and one or more microphones 100.

In various embodiments, drivers 80 may be moving coil drivers, balanced armature drivers or any other suitable drivers. Although FIGS. 3-5 and 8 illustrate using two drivers 80, more or less drivers 80 are contemplated. Drivers 80 may be secured within the housing 120, 40 with driver caps 90 and/or driver plugs or mounts 70, for example. In certain embodiment, drivers 80 are coupled to stimulus channels 65 as illustrated in FIG. 8, for example. Certain embodiments provide drivers 80 coupled to driver tubes 60 via driver plugs 70 as illustrated in FIGS. 3-5, for example. Drivers 80 are sound transducers that generate acoustic signals from the electrical test signals received via cable 150. The stimulus channels 65 or driver tubes 60 are operable to carry the acoustic stimulus generated by drivers 80 to probe tube 30, which carries the acoustic stimulus into an ear canal. Stimulus channels 65 or driver tubes 60 may include one or more acoustic dampers 50 and/or other suitable filters for tuning or adjusting the tonal balance of the acoustic stimuli generated by drivers 80.

In certain embodiments, the probe tube 30 includes separate sound channels for carrying acoustic stimulus from each of the drivers 80 via stimulus channels 65 or driver tubes 60. Each of the acoustic stimulus sound channels comprises one or more stimulus lumens 32. Additionally, the probe tube 30 includes one or more microphone lumens 31 forming an acoustic microphone sound channel for communicating the acoustic condition of the ear canal to one or more microphones 100.

Figure 6:
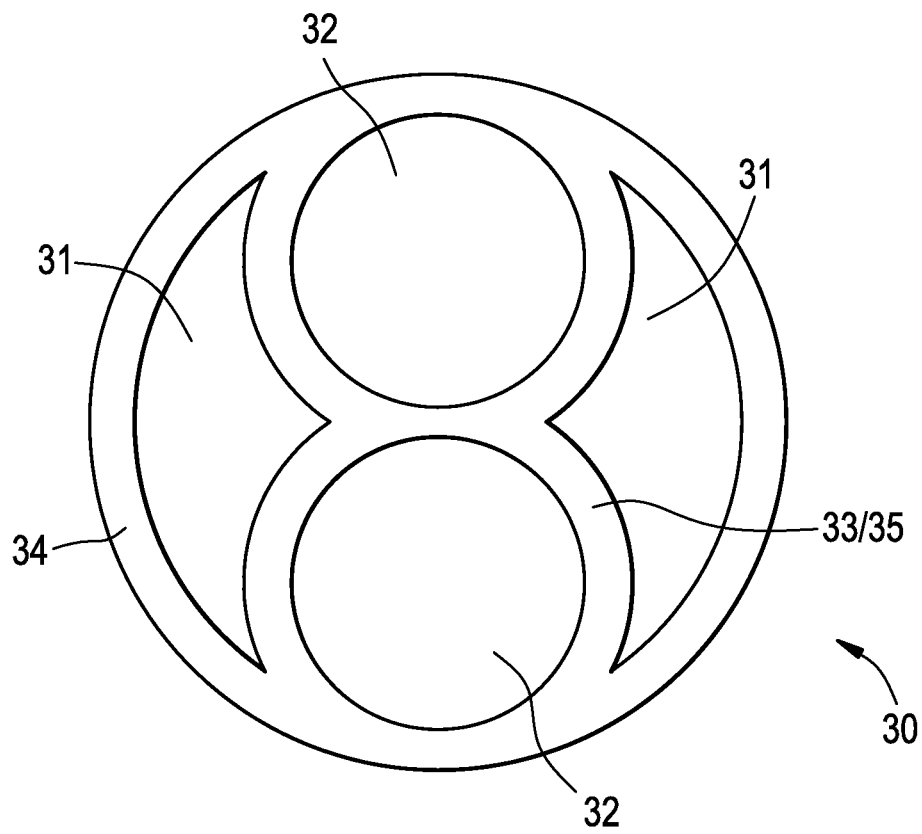
FIG. 6 illustrates a cross-sectional view of an exemplary embodiment of a probe tube used in accordance with an embodiment of the present technology.
Figure 10:
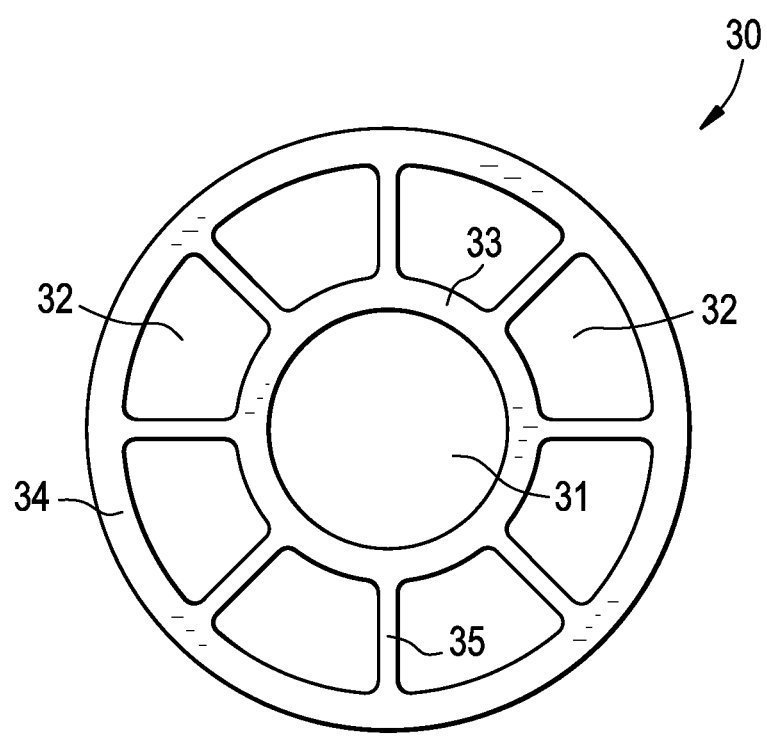
FIG. 10 illustrates a cross-sectional view of an exemplary embodiment of a probe tube used in accordance with an embodiment of the present technology.
Figure 11:
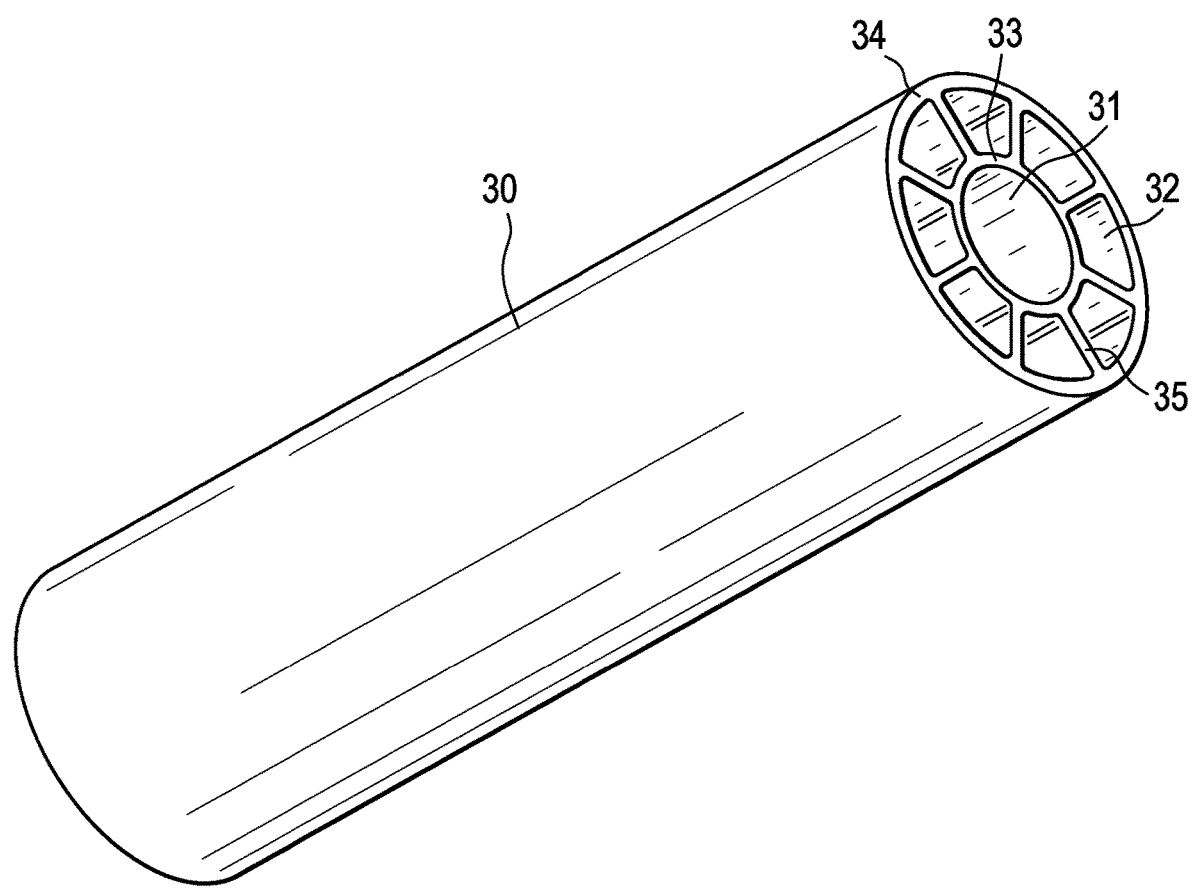
FIG. 11 illustrates an isometric view of an exemplary embodiment of a probe tube used in accordance with an embodiment of the present technology.
Figure 16:
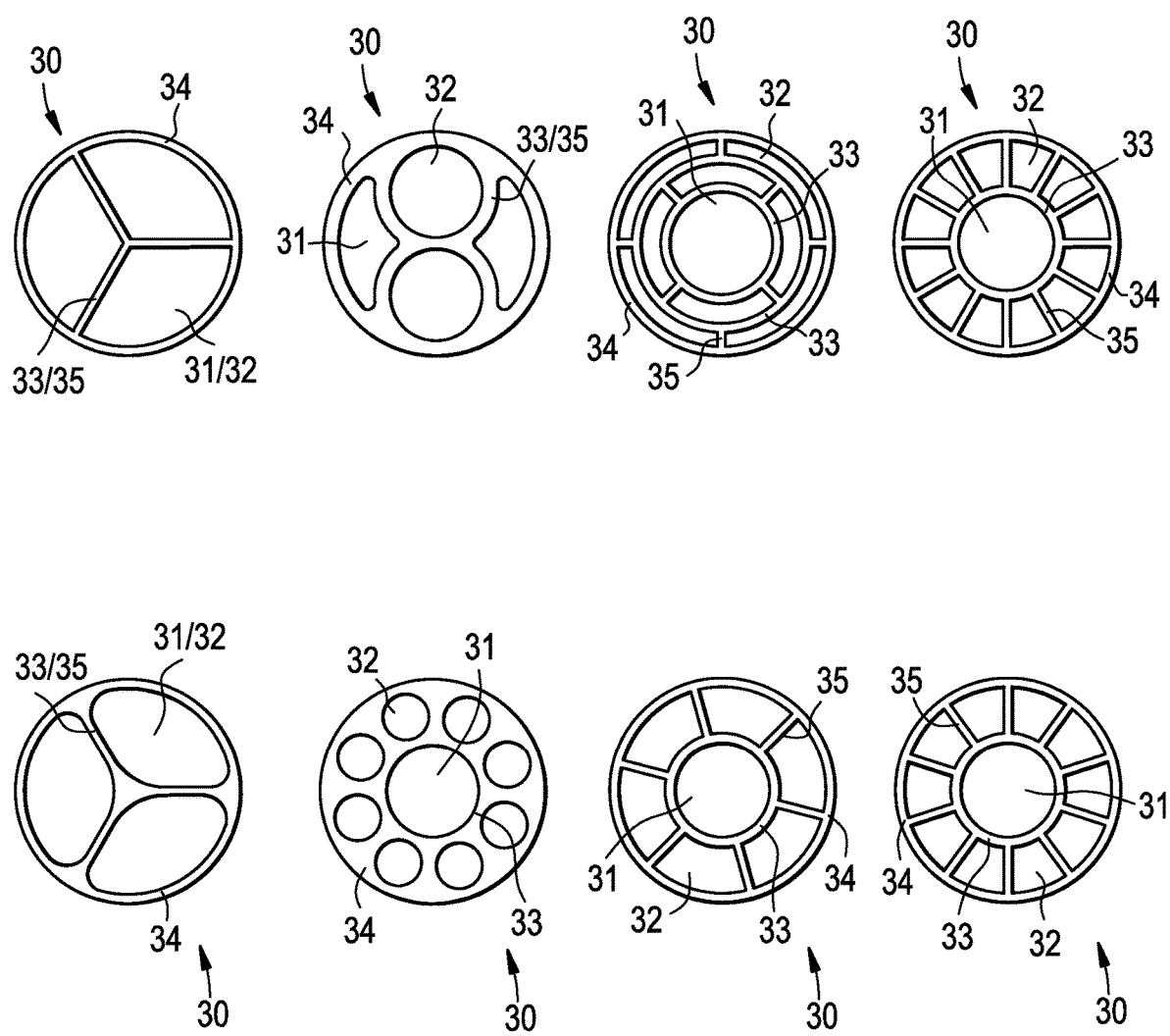
FIG. 16 illustrates cross-sectional views of exemplary embodiments of probe tubes used in accordance with an embodiment of the present technology.

FIGS. 6 and 10 illustrate cross-sectional views of exemplary embodiments of a probe tube 30 used in accordance with an embodiment of the present technology. FIG. 11 illustrates an isometric view of an exemplary embodiment of a probe tube 30. FIG. 16 illustrates cross-sectional views of exemplary embodiments of probe tubes 30.

Referring to FIGS. 6, 10-11 and 16, certain embodiments provide that the probe tube 30 is produced by an extrusion process using a thermoplastic elastomer, such that the probe tube 30 is both disposable and inexpensive. The thermoplastic elastomer may be a polyether block amide (trade name PEBAX™), for example, with a net durometer of 72 Shore A, among other things. In certain embodiments, the probe tube 30 may be produced by injection molding or plastic forming, however, these processes typically entail a significantly increased cost per part produced. In various embodiments, other materials such as plastic or rubber, among other things, could be used for the extrusion.

Figure 2:
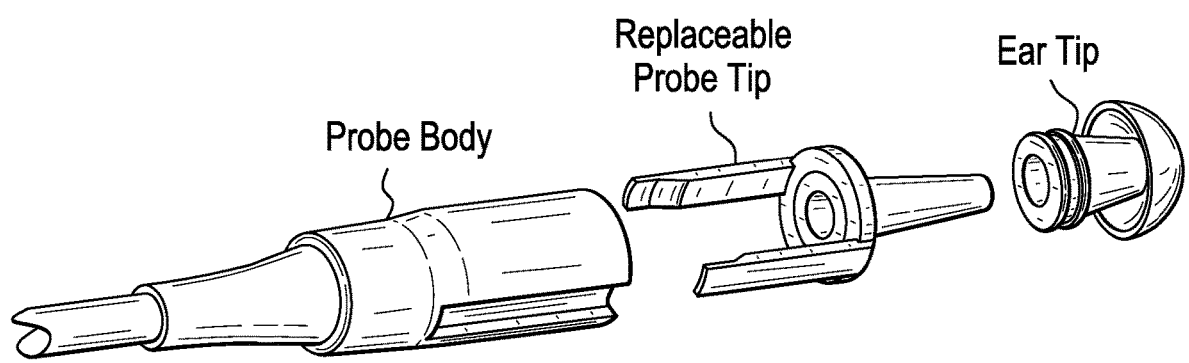
FIG. 2 illustrates an exploded view of an exemplary replaceable probe tip design as is known in the art.

In order to accommodate common industry standard eartips 20 and fitting into ear canals of infants, probe tube 30 terminates at the ear canal end in a maximum diameter of approximately three millimeters. As such, the acoustic stimulus and microphone channels are brought to the ear canal with a smaller cross-sectional area than would be desired to provide wideband acoustic stimulus with a flat frequency response. Replaceable probe interfaces, as illustrated in FIG. 2, for example, are commonly made from injection molded plastic or extruded silicone tubing. In these designs a large portion of the overall available cross-sectional area of the three millimeter diameter is consumed by the material of which the interface component is made because of limitations in wall thicknesses that can be produced using common plastic injection molding processes or silicone extrusion processes. The area consumed by the material in one popular design using a silicone extrusion process is over 60% of the total area of the tube. In another popular design using plastic injection molding, the plastic walls forming the channels consumes over 70% of the available area.

Certain embodiments provide that probe tube 30 has a cross-sectional area lost to the material that is less than 40%, allowing a significant increase in the cross-sectional area allotted to the acoustic stimulus and microphone channels and thus providing an improved acoustic performance. The improved acoustic performance may be due to, for example, the use of an extrusion process that can consistently extrude wall thicknesses in a range between 0.07 and 0.30 millimeters (0.003 to 0.010 inches) or more specifically, approximately 0.12 millimeters (0.005 inches). Typical plastic injection molding processes have minimum wall thicknesses of 0.50 millimeter (0.020 inches) and silicone extrusion requires a large wall in order to maintain its shape because of its significantly lower durometer.

Various embodiments provide a probe tube 30 with a reduced outer wall 34 thickness, radial wall 35 thickness, and inner wall 33 thickness such that the effective total acoustic tube area is increased while maintaining the outer diameter of the probe tube 30.

Replaceable interface components 30 in existing hearing testing probes 10 are typically keyed 36 or unidirectional in their connection to the probe body 40. This requires that a user orient the probe tube 30 in a particular fashion in order to properly mate the probe tube 30 with the probe body 40. Certain embodiments provide that the probe tube 30 is of a symmetrical design as illustrated in FIGS. 10-11, for example, allowing the probe tube 30 to be placed onto the probe body 40 by simply lining up the probe tube 30 end with the entrance port on the probe body 40. The symmetrical design illustrated in FIGS. 10-11, for example, allows the user to replace the probe tube 30 without regards to orientation, significantly simplifying the process and making it easier to perform in low light environments or by individuals with impaired vision.

Referring to FIGS. 10-11, one of the disclosed symmetrical designs provides eight stimulus lumens 32 located circumferentially about the center microphone lumen 31. Each of these stimulus lumens 32 is defined by two radial walls 35 extending from the center microphone lumen 31 defined by inner wall 33 to the outside wall 34 of the probe tube 30. In various embodiments, eight of these radial walls 35 are evenly spaced about the diameter to create the eight individual stimulus lumens 32. In certain embodiments, four adjoining stimulus lumens 32 are used to form two acoustic stimulus sound channels for receiving stimulus from the corresponding two stimulus channels 65.

Figure 12:
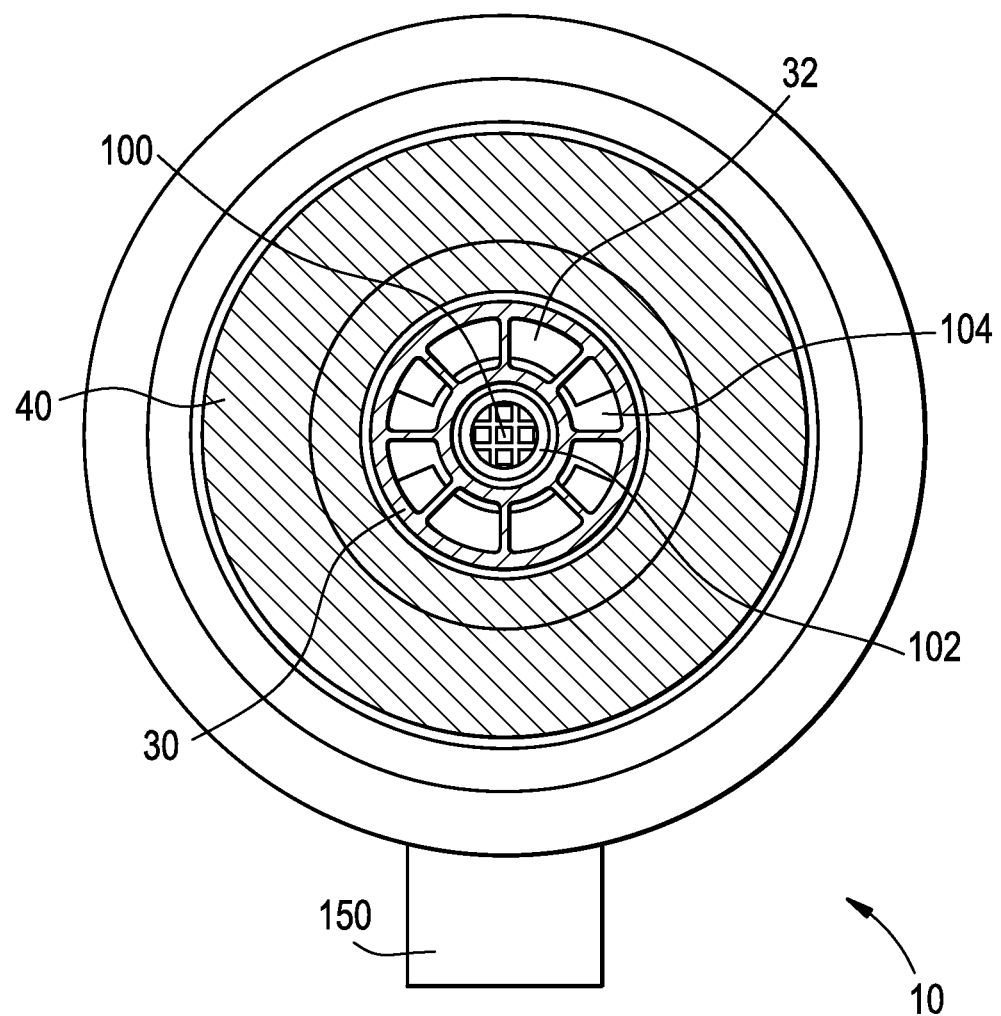
FIG. 12 illustrates a cutaway view of an exemplary sealing and mating surface of a hearing testing probe and probe tube used in accordance with an embodiment of the present technology.
Figure 13:
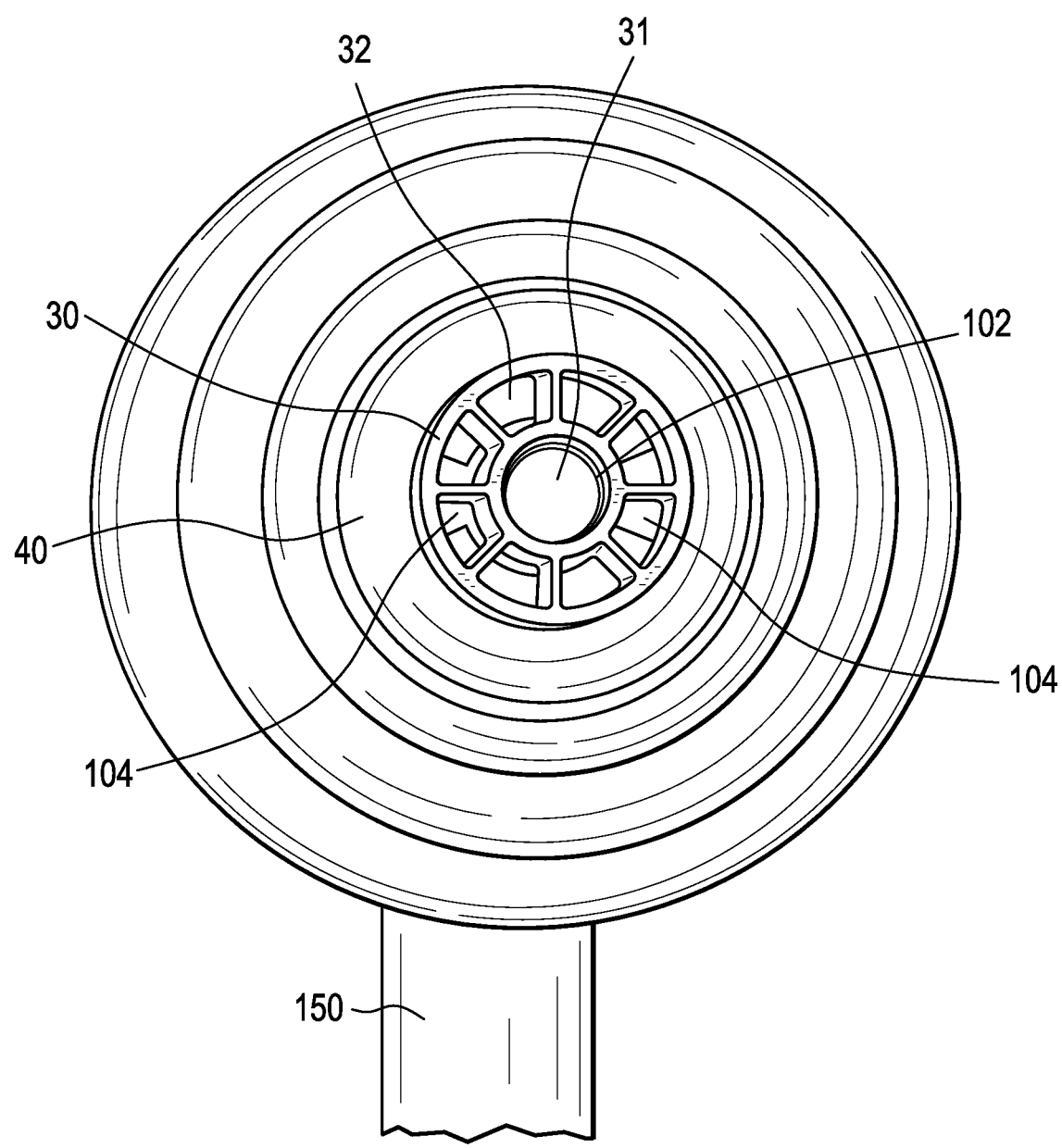
FIG. 13 illustrates an exemplary sealing and mating surface of a hearing testing probe and probe tube used in accordance with an embodiment of the present technology.

FIGS. 12-13 illustrate views of an exemplary sealing and mating surface 104 of a hearing testing probe 10 and probe tube 30 used in accordance with an embodiment of the present technology. The sealing and mating surface 104 of the hearing testing probe 10 provides a seal that extends across the midline on the profile of the probe tube 30, between the central microphone lumen 31 and the outside wall 34 of the probe tube 30, to separate and isolate two groups of four adjacent stimulus lumens 32. The sealing and mating surface 104 is of sufficient width to ensure complete contact across one of the radial walls 35 which define the stimulus lumen 32, regardless of the orientation of the probe tube 30 relative to the sealing and mating surface 104. The sealing and mating surface 104 used as described above ensures that each acoustic stimulus sound channel has four of the stimulus lumens 32, maximizing the effective area of each acoustic stimulus sound channel. In certain embodiments, the sealing and mating surface 104 may comprise a microphone bracket as illustrated in FIGS. 7-9, among other things.

Referring to some of the embodiments illustrated in FIG. 16 in comparison to the embodiment illustrated in FIG. 10, for example, more or less radial walls 35 may be used to divide the area into more or less individual stimulus lumens 32. The embodiment illustrated in FIG. 10, for example, provides for eight of the stimulus lumen 32 based on existing thermoplastic extrusion technology which allows for extruded wall thicknesses of approximately 0.12 millimeters (0.005 inches). Because the width of the sealing and mating surface 104 on the probe 10 is proportional to the width of each stimulus lumen 32, a probe tube 30 with six or less stimulus lumen 32 may provide a reduced acoustic path due to a larger sealing and mating surface 104. Inversely, a probe tube 30 with ten or more stimulus lumen 32 may have a reduced effective acoustic path due to the increased area consumed by the greater number of radial walls 35.

Eartips 20 are typically applied to hearing testing probes 10 to provide a conforming, sealing, and comfortable fit to a subject's ear canal. The seal provided by an eartip 20 excludes ambient noise and/or provides a pressure seal during audiometric testing. Users of hearing testing equipment may have preferences for particular eartips 20 or type of eartips 20 based on numerous factors. One factor may be the testing environment, which may require an eartip 20 to provide a particular level of sound attenuation in order to perform adequately. Another factor may be patient comfort, where choice of eartip design and construction may influence the comfort of the eartip 20 to an ear canal. A significant factor is often the cost of the eartip 20 per test. A single-use disposable eartip 20 is often more costly than a cleanable reusable eartip design.

The probe tube 30 is configured for use with an eartip 20, such as industry-standard elastomeric eartips 20, single-use disposable eartips 20, or any other suitable eartips 20. The probe tube 30 has an outer diameter. In various embodiment, the outer diameter of the probe tube 30 is appropriate to mate and seal with the central channel found on industry-standard elastomeric eartips 20 and the like, such that the probe tube 30 provides compatibility with many of the eartips 20 that users of the hearing test probe 10 may prefer. Certain embodiments provide for use of single-use disposable eartips 20. The single-use eartip 20 may be bonded directly to the probe tube 30 to provide a single disposable assembly, as illustrated in FIG. 15, for example.

Certain embodiments provide that the probe tube 30 aligns flush with, or extends slightly beyond (e.g., two to three millimeters), the ear canal end of eartip 20 to increase the accuracy of calibration of the hearing testing probe.

FIG. 17 illustrates cross-sectional views of exemplary embodiments of keyed 36 probe tubes 30 used in accordance with an embodiment of the present technology. Certain embodiments provide one or more keys 36 operable to prevent a user from applying eartip 20 types other than those specifically designed for use with such embodiment. Keyed 36 probe tubes 30 may be desirable, for example, if a manufacturer prefers to require users to purchase specific eartips 20. As an example, keyed 36 probe tubes 30 may ensure the use of eartips 20 that have specific design details for providing proper performance of the intended audiometric test, to limit compatibility with competitive instrumentation, or to ensure sales of the manufacturer's eartips 20.

Referring again to FIG. 17, examples of keyed 36 probe tubes 30 are provided that may comprise, for example, a notch 36 indented into the outer diameter of the extrusion. The notch 36 may prevent standard eartips 20 from creating a seal to the subject's ear canal, preventing completion of an audiometric test. A notch or cutaway may comprise a single detail or may be comprised of several notches around the perimeter of the probe tube 30. In various embodiments, a key 36 may comprise one or more details extending outside the perimeter of the probe tube 30 for causing interference in the center channel of an eartip 20 incompatible with the probe tube 30.

Referring again to FIGS. 3-6, various embodiments provide that the probe tube 30 detachably couples at a first end to the driver tubes 60 within probe body 40. In certain embodiments, such as when using an asymmetrical probe tube 30 as illustrated in FIG. 6, for example, one or more of the probe tube 30 and the probe body 40 may include visual and/or mechanical keys for properly aligning the probe tube 30 with the driver tubes 60. For example, the probe tube 30 and probe body 40 may include a marking at the top or along the length of each of the probe tube 30 and the probe body 40 to indicate the proper alignment when inserting the probe tube 30 into the probe body 40 for coupling with the driver tubes 60. As another example, the probe tube 30 and probe body 40 may include one or more keys 36, as discussed above with regard to FIG. 17, for dictating the proper alignment when inserting the probe tube 30 into the probe body 40 for coupling with the driver tubes 60. Certain embodiments may use any suitable mechanism for assisting in the alignment of the probe tube 30 with the driver tubes 60. The scope of various aspects of the present invention should not be limited by the alignment mechanism, unless explicitly claimed.

In certain embodiments, when the probe 10 is fully assembled, a second end of the probe tube 30 extends through a hole in the center of an eartip 20 and aligns flush with, or extends slightly beyond (e.g., two to three millimeters), the face of the eartip 20. The eartip 20 is held in place by a front tapered section of the probe body 40, with the second end of the probe tube 30 acoustically sealing to the eartip 20 at the ear canal end of the eartip 20. The eartip 20 may be removed from the probe body 40 without removing the probe tube 30. The eartip 20 may be made of an elastic material, such as, for example, rubber or any other suitable material. Various eartips 20 with the same inner hole diameter but with varying outer sizes may be used with the probe 10. For example, an eartip 20 with a smaller outer size may be used when performing a hearing test on an infant while an eartip 20 with a larger outer size may be used when performing a hearing test on an adult.

In various embodiments, the probe tube 30 may be replaceable and/or disposable without having to replace/dispose of the probe body 40 and/or the eartip 20. For example, if cerumen or other biological material contaminates the probe tube 30, a user may replace the contaminated probe tube 30 with a new and/or uncontaminated probe tube 30 so that an accurate measurement may be achieved. In certain embodiments, such as discussed above with regard to FIG. 15, single-use disposable eartips 20 may be used. For example, the single-use eartip 20 may be bonded directly to the probe tube 30 to provide a single disposable assembly as illustrated in FIG. 15.

Referring again to FIGS. 3-6, one or more microphones 100 may be housed within end cap 120 and/or probe body 40 for receiving the acoustic response from the ear canal via probe tube 30. In an embodiment, an open area between the one or more microphones 100 and the one or more microphone lumens 31 of the probe tube 30 may allow all of the one or more microphones to receive sound from all of the one or more microphone lumens 31 of the probe tube 30. For example, if the probe 10 has two microphones 100 and the probe tube 30 has two microphone lumens 31 for carrying the acoustic response from the ear canal to the two microphones 100, both of the microphones 100 receive the acoustic response from both of the microphone lumens 31 of the probe tube 30. A flex circuit 110 coupled to the one or more microphones 100 may communicate the electrical output from the one or more microphones 100 from the probe 10 via cable 150.

Referring again to FIGS. 7-15, various embodiments provide that the probe tube 30 detachably couples at a first end to the stimulus channels 65 via sealing and mating surface 104 within probe body 40. In certain embodiments, the microphone lumen 31 of the probe tube 30 may be received by a microphone tube 102 at the probe body 40. The microphone tube 102 attaches to one or more microphones 100 at a first end, and extends, at least partially, into microphone lumen 31 at a second end when the probe tube 30 is coupled within probe body 40 as illustrated in FIGS. 7-8, for example. The one or more microphones 100 may be housed within end cap 120 and/or probe body 40 for receiving the acoustic response from the ear canal via probe tube 30 and microphone tube 102. In various embodiments, when the probe 10 is fully assembled, a second end of the probe tube 30 extends through a hole in the center of an eartip 20 and aligns flush with, or extends slightly beyond (e.g., two to three millimeters), the face of the eartip 20.

Certain embodiments provide that the eartip 20 is held in place by a front tapered section of the probe body 40, with the second end of the probe tube 30 acoustically sealing to the eartip 20 at the ear canal end of the eartip 20 as illustrated in FIG. 14, for example. The eartip 20 may be removed from the probe body 40 without removing the probe tube 30. The eartip 20 may be made of an elastic material, such as, for example, rubber or any other suitable material. Various eartips 20 with the same inner hole diameter but with varying outer sizes may be used with the probe 10. For example, an eartip 20 with a smaller outer size may be used when performing a hearing test on an infant while an eartip 20 with a larger outer size may be used when performing a hearing test on an adult.

In various embodiments, the probe tube 30 may be replaceable and/or disposable without having to replace/dispose of the probe body 40 and/or the eartip 20. For example, if cerumen or other biological material contaminates the probe tube 30, a user may replace the contaminated probe tube 30 with a new and/or uncontaminated probe tube 30 so that an accurate measurement may be achieved. In certain embodiments, such as discussed above with regard to FIG. 15, single-use disposable eartips 20 may be used. For example, the single-use eartip 20 may be bonded directly to the probe tube 30 to provide a single disposable assembly as illustrated in FIG. 15.

Figure 18:
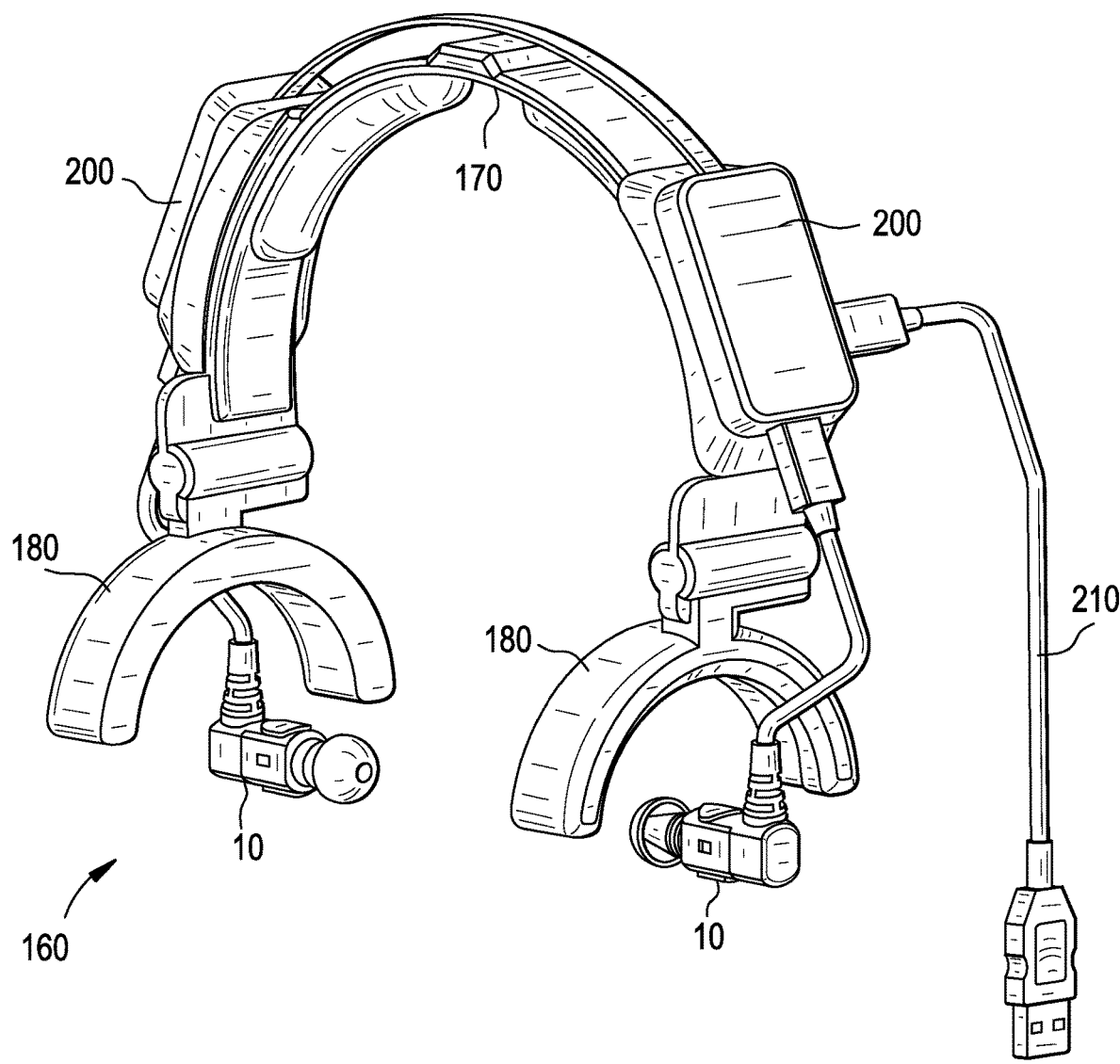
FIG. 18 illustrates a side view of an exemplary embodiment of a hearing testing probe headset used in accordance with an embodiment of the present technology.

FIG. 18 illustrates a side view of an exemplary embodiment of a hearing testing probe headset 160 used in accordance with an embodiment of the present technology. Certain embodiments of the hearing testing probe headset 160 include a headband 170 and an attached ear wrap component 180 for securely fastening to a user's head and correctly orienting hearing testing probes 10 into a user's ears. Additionally, the headband 170 is operable to securely mount one or more digital interfaces 200 to the headband 170. By mounting the one or more digital interfaces 200 to the headband 170, the weight of the digital interfaces 200 and/or any tension on the cable 210 attached to the digital interfaces 200 will not cause the hearing test probes 10 to be pulled from a user's ears.

In various embodiments, when secured to a user, the headband 170 of the hearing testing probe headset 160 curves around the top and sides of the user's head and the ear wrap component 180 fits snugly above and partially around a user's ears. The headband 170 and attached ear wrap component 180 may be adjustable to accommodate different sizes and shapes of a user's head and the positioning of the user's ears in relation to the user's head. For example, the headband 170 may extend or contract to be longer or shorter based on a user's fit preferences. As another example, the ear wrap component 180 may tighten inward or loosen outward based on a user's fit preferences.

Figure 19:
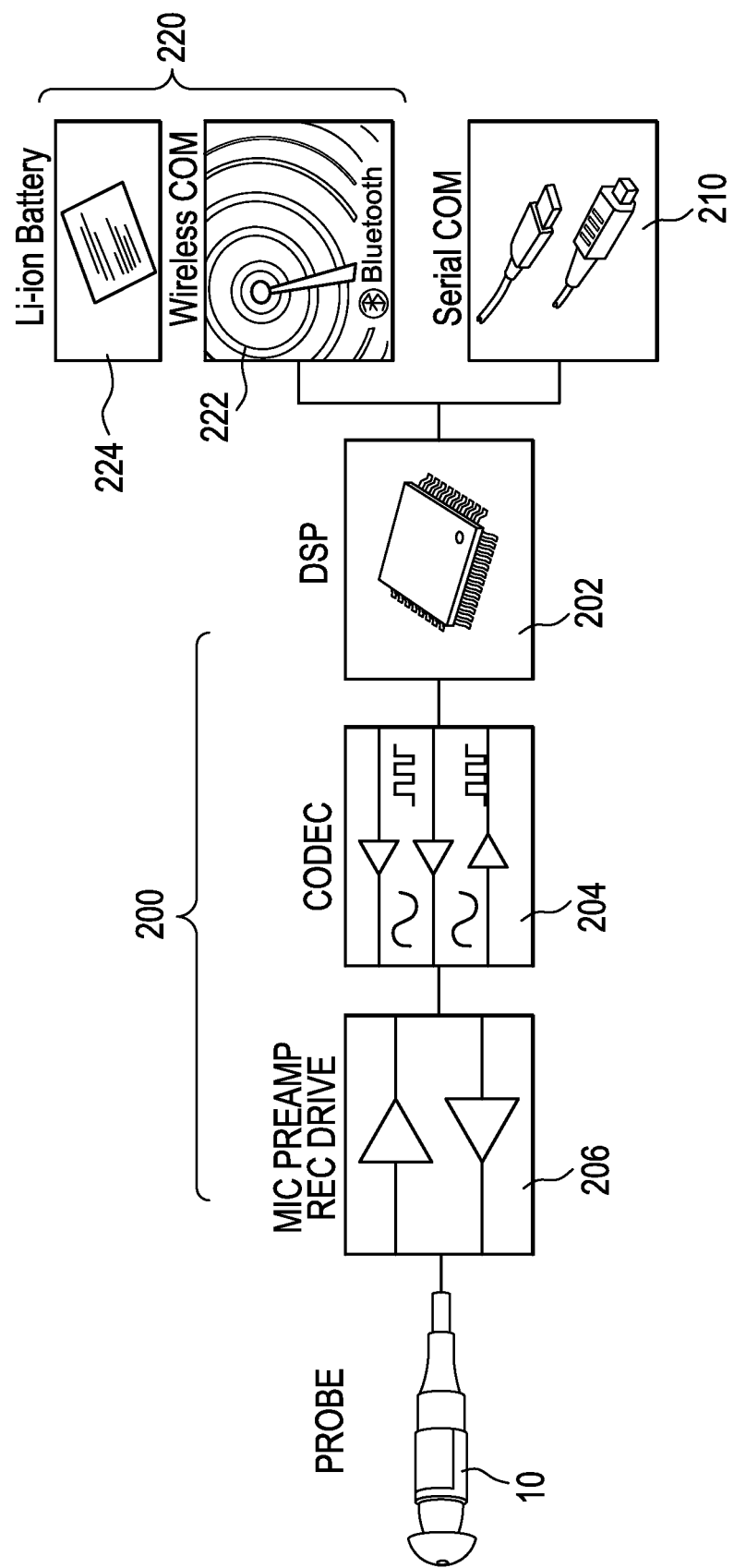
FIG. 19 illustrates a block diagram of an exemplary embodiment of a digital interface used in accordance with an embodiment of the present technology.

FIG. 19 illustrates an exemplary block diagram of an embodiment of an exemplary digital interface 200 used in accordance with an embodiment of the present technology. Certain embodiments of the digital interface 200 include a digital signal processor (DSP) 202, a CODEC 204 (i.e., an analog to digital and digital to analog converter) and a microphone preamplifier/receiver driver 206.

In certain embodiments, the digital interface 200 may transmit analog test signals, among other things, to the drivers 80 of hearing testing probe 10 via cable 150, for example. The digital interface 200 may receive electrical response signals, among other things, from the hearing testing probe 10 via cable 150, for example. In certain embodiments, the digital interface 200 is not limited to communicating with a hearing testing probe 10. Instead, the digital interface 200 may transmit analog test signals and receive electrical response signals from any suitable device such as, for example, an auditory brainstem response (ABR) test system, among other things.

In various embodiments, the digital interface 200 may include at least one data port (not shown) for communicating digital signals with a hearing test system. The hearing test system may be a computer, for example, among other things. The at least one data port may be operable to receive a digital cable 210, such as, for example, USB, FireWire, and the like. Alternatively or additionally, a wireless module 220 may be plugged into the at least one data port. The wireless module includes a wireless transceiver 222 for transmitting and receiving digital signals between the digital interface 200 and the hearing test system. The wireless transceiver 222 may be operable to communicate over any suitable network, such as, for example, Bluetooth, Wi-Fi, cellular networks, among others. In certain embodiments, the wireless module 220 may be battery-powered 224. For example, the wireless module 220 may include a lithium-ion battery 224 or any other suitable battery. In certain embodiments, the same data port may be used for either receiving a digital cable 210 or a wireless module 220 depending on whether the user prefers to communicate by a wired or a wireless connection.

In certain embodiments, the DSP 202 may receive the test signals from the hearing test system in a digital format. The DSP 202 then provides the test signals to the CODEC 204, which converts the digital test signals to analog test signals and drives the receivers 80 in the probe 10. Alternatively or additionally, the DSP 202 may generate the test signals upon receipt of specific commands from the hearing test system. The commands received from the hearing test system dictate the stimulus type, for example, noise, pure-tones, or clicks, as well as frequency, duration, intensity, and any other suitable qualifiers. The DSP 202 generates the requested test signals and provides the digital test signals to the CODEC 204, which converts the digital test signals to analog test signals and drives the receivers 80 in the probe 10.

In various embodiments, the DSP 202 may provide a probe fit test function that generates a test tone sequence through the attached probe 10 and monitors the response to determine when the probe 10 is properly fit into an ear canal. The DSP 202 can initiate the intended hearing test function upon detection of the proper fit, or may communicate this status to the hearing test system.

In certain embodiments, test signal information may be downloaded or uploaded from the hearing test system to memory at the digital interface 200. Once the probe 10 is in position and the user is ready for the test to begin, the DSP 202 may retrieve the test signal information from memory and generate the appropriate test signals to conduct the hearing test. In certain embodiments, a connection between the digital interface 200 and the hearing test system may not be necessary while performing the hearing test. For example, the digital interface 200 may be connected with the hearing test system via a wired or wireless connection when receiving test signal information or any other suitable information (i.e., before the hearing test and/or at the beginning of the hearing test) and when transmitting measured response signals from the hearing test or any other suitable information (i.e., after the hearing test and/or at the end of the hearing test). As such, certain embodiments provide for a connection between the digital interface 200 and the hearing test system when the connection is needed to communicate data between the digital interface 200 and the hearing test system.

In various embodiments, the test signal generation by the DSP 202 may be initiated through a predetermined command received from a connected hearing test system. The received commands may specify, for example, the type of test signal(s) to be generated, such as pure-tones, noises, clicks, or any other suitable test signal. The received commands may further specify, for example, the frequency, duration, intensity, and any other suitable information for generating the test signals. The digital interface 200 may allow for the upload of a custom test signal waveform or series of waveforms. The digital interface 200 may also accept a series of waveform commands that allows for an autonomous run of a multi-frequency and/or multi-test function.

In certain embodiments, the digital interface 200 may receive a measured response signal from a probe 10, an electrode or any other suitable apparatus. In certain embodiments, the DSP 202 receives the measured response signal pre-amplified by the preamplifier 206 and converted from analog to digital by the CODEC 204. The DSP 202 may store the measured response signal stream for a particular period of time in its internal digital memory or in an attached storage device. For example, if a connection (i.e., wired or wireless) between the digital interface 200 and the hearing test system is not currently established, the DSP 202 may store the measured response signal stream until a connection is established with the hearing test system. Alternatively or additionally, if a connection (i.e., wired or wireless) between the digital interface 200 and the hearing test system is currently established, the duration of the measured response signal stream buffering may be determined by function calls from the hearing test system or in any other suitable manner.

In certain embodiments, the DSP 202 may also provide signal processing functions such as averaging, filtering, noise-reduction, artifact rejection, and/or any other suitable signal processing or analysis functions. The signal processing may be determined by function calls from the hearing test system or in any other suitable manner. The raw or processed measured response signal stream is sent from the digital interface 200 to the hearing test system via a wired 210 or wireless 220 connection. Other DSP 202 advanced analysis functions may include otoacoustic emission measurement, transfer function measurement, leak detection, cavity volume measurement, acoustic reflex measurement, acoustic reflectance measurement, as well as any other suitable advanced algorithms.

Certain embodiments provide a digital interface 200 coupled to the hearing testing probe 10 to allow for the use of a lightweight digital cable 210 and/or a wireless interface 220. The use of digital transmission provides for greater flexibility in cable lengths, less bulky cables, fewer problems of signal degradation and RF interference. The digital interface 200 also allows for the use of wireless transmission, providing greater flexibility in testing environments and eliminating the need for a tethered connection.

Certain embodiments provide a replaceable/disposable low-cost probe tube design that separates the probe tube 30 from the eartip 20, so that the probe tube 30 may be replaced when contaminated. The eartip 20 is held in place by the front tapered section of the probe body 40, with the probe tube 30 acoustically sealing to the eartip 20 at the ear canal end. The eartip 20 can be removed without removing the probe tube 30. A contaminated probe tube 30 is easily replaced by the user of the hearing testing probe 10. Certain embodiments provide an inexpensive solution to frequent probe tube 30 replacement, while providing a solution for extending the probe tubes 30 flush to, or slightly beyond (e.g., two to three millimeters), the face of eartip 20.

Various embodiments provide a hearing testing probe apparatus 10. The hearing testing probe apparatus 10 comprises a plurality of drivers 80 within a probe body 40 operable to generate test stimulus from received test signals. The hearing testing probe apparatus 10 comprises one or more microphones 100 within the probe body 40 operable to receive at least one measured response. The hearing testing probe apparatus 10 comprises a plurality of stimulus channels 65 within the probe body 40 operable to carry the generated test stimulus from the plurality of drivers 80. Each of the plurality of stimulus channels 65 is coupled to a separate one of the plurality of drivers 80. The hearing testing probe apparatus 10 comprises a probe tube 30 detachably coupled at a first end to the plurality of stimulus channels 65 within the probe body 40. The probe tube 30 extends through a center hole in an eartip 20 to align flush to, or extend slightly beyond, an ear canal end of the eartip 20 at a second end. The probe tube 30 comprises a plurality of separate stimulus lumens 32 corresponding to each of the plurality of stimulus channels 65 for receiving and carrying the generated test stimulus from the first end of the probe tube 30 for output from the second end of the probe tube 30. The probe tube 30 comprises one or more separate microphone lumens 31 for receiving and carrying the one or more measured responses received at the second end of the probe tube 30 to the one or more microphones 100 at the first end of the probe tube 30.

In an embodiment, the hearing testing probe apparatus 10 comprises a sealing and mating surface 104. The probe tube 30 is detachably coupled at the first end to the plurality of stimulus channels 65 at the sealing and mating surface 104 within the probe body 40.

In an embodiment, the eartip 20 is detachably coupled to the probe body 40.

In an embodiment, the probe tube 30 is removable from the eartip 20.

In an embodiment, the eartip 20 is bonded directly to the probe tube 30 to provide a single assembly.

In an embodiment, the single assembly is a single-use disposable component.

In an embodiment, the probe tube 30 is operably attached to the hearing testing probe 10 irrespective of the orientation about a longitudinal axis of the probe tube 30.

In an embodiment, the one or more separate microphone lumens 31 and the plurality of separate stimulus lumens 32 are configured symmetrically within the probe tube 30.

In an embodiment, the one or more separate microphone lumens 31 comprises a cylindrical central lumen defined by an inner wall 33 within the probe tube 30.

In an embodiment, the plurality of separate stimulus lumens 32 are located circumferentially about the cylindrical central lumen 31. Each of the plurality of separate stimulus lumens 32 are defined by two radial walls 35 extending from the inner wall 33 to an outer wall 34 within the probe tube 30.

In an embodiment, the probe tube 30 comprises eight radial walls 35 extending from the inner wall 33 to the outer wall 34 within the probe tube 30 such that the plurality of separate stimulus lumens 32 is eight lumens.

In an embodiment, the probe tube 30 comprises an inner wall 33, an outer wall 34 and a plurality of radial walls 35.

In an embodiment, the cross-sectional area of the inner wall 33, the outer wall 34 and the plurality of radial walls 35 is less than 40%.

In an embodiment, the thickness of the inner wall 33, the outer wall 34 and the plurality of radial walls 35 is approximately 0.012 millimeters (0.005 inches).

In an embodiment, the probe tube 30 is extruded using a thermoplastic elastomer.

In an embodiment, a net durometer of the thermoplastic elastomer is 72 Shore A.

In an embodiment, the hearing testing probe apparatus 10 comprises one or more microphone tubes 102 operably attached at a first end to the one or more microphones 100, and extending into the one or more separate microphone lumens 31 when the probe tube 30 is coupled within the probe body 40.

Various embodiments provide a hearing testing probe apparatus 10. The hearing testing probe apparatus 10 comprises a probe tube 30 detachably coupled at a first end to a probe body 40 and extending through a center hole in an eartip 20 to align proximate a face of the eartip 20 at a second end. The probe tube 30 comprises a plurality of stimulus lumens 32 for receiving and carrying stimulus from the first end of the probe tube 30 for output at the second end of the probe tube 30. The probe tube 30 comprises one or more microphone lumens 31 for receiving and carrying one or more measured responses from the second end of the probe tube 30 to one or more microphones 100 at the first end of the probe tube 30.

In an embodiment, the probe tube 30 is operably attached to the hearing testing probe 10 irrespective of the orientation about a longitudinal axis of the probe tube 30.

In an embodiment, the probe tube 30 is fixably attached to the eartip 20 to form a single entity, wherein the single entity is a single-use disposable component.

In an embodiment, the one or more microphone lumens 31 are a central receiving lumen and the plurality of stimulus lumens 32 are located peripherally to the one or more microphone lumens 31. The one or more microphone lumens are operable to form one or more distinct receiving channels for receiving the one or more measured responses. The plurality of stimulus lumens 32 are operable to form one or more transmitting channels for transmitting the stimulus.

In an embodiment, the probe tube 30 terminates flush at, or extends slightly beyond, an ear canal end of the eartip 20.

While particular elements, embodiments and applications of the present invention have been shown and described, it will be understood that the invention is not limited thereto since modifications can be made by those skilled in the art without departing from the scope of the present disclosure, particularly in light of the foregoing teachings.

What is claimed is:

1. A probe tube comprising:
    an outer tube wall extending from an open proximal end to an open distal end, wherein the outer tube wall comprises a constant outer diameter;
    a plurality of stimulus lumens extending within the outer tube wall from the open proximal end to the open distal end of the probe tube, the plurality of stimulus lumens operable to receive and carry a stimulus from the open proximal end of the probe tube for output at the open distal end of the probe tube; and
    at least one microphone lumen extending within the outer tube wall from the open proximal end to the open distal end of the probe tube, the at least one microphone lumen operable to receive and carry at least one measured response from the open distal end of the probe tube for output at the open proximal end of the probe tube,
    wherein the plurality of stimulus lumens and the at least one microphone lumen are arranged symmetrically within the outer tube wall, the outer tube wall enclosed between the open proximal end and the open distal end, and
    wherein the probe tube comprises a rigidity such that a shape of the probe tube is maintained when inserted in an eartip.

2. The probe tube of claim 1, wherein the eartip is detachably coupled to the probe tube.

3. The probe tube of claim 1, wherein the eartip is bonded directly to the probe tube to provide a single assembly.

4. The probe tube of claim 3, wherein the single assembly is a single-use disposable component.

5. The probe tube of claim 1, wherein the probe tube is operably attached to a hearing testing probe irrespective of the orientation about a longitudinal axis of the probe tube.

6. The probe tube of claim 1, wherein the outer tube wall is a uniform thickness.

7. The probe tube of claim 6, wherein the at least one microphone lumen comprises a cylindrical central lumen defined by an inner wall within the outer tube wall.

8. The probe tube of claim 7, wherein the plurality of stimulus lumens are located circumferentially about the cylindrical central lumen, each of the plurality of stimulus lumens being defined by two radial walls extending from the inner wall to the outer tube wall.

9. The probe tube of claim 8, wherein the probe tube comprises eight radial walls extending from the inner wall to the outer tube wall such that the plurality of stimulus lumens is eight lumens.

10. The probe tube of claim 1, wherein the probe tube comprises an inner wall and a plurality of radial walls, the inner wall and the plurality of radial walls within the outer tube wall.

11. The probe tube of claim 10, wherein a cross-sectional area of the inner wall, the outer tube wall and the plurality of radial walls is less than 40% of a total cross-sectional area of the probe tube.

12. The probe tube of claim 10, wherein the thickness of the inner wall, the outer tube wall and the plurality of radial walls is approximately 0.012 millimeters (0.005 inches).

13. The probe tube of claim 1, wherein the probe tube is extruded using a thermoplastic elastomer.

14. The probe tube of claim 13, wherein a net durometer of the thermoplastic elastomer is 72 Shore A.

15. The probe tube of claim 1, wherein the eartip is coupled to the probe tube, and wherein the open distal end of the probe tube aligns flush to, or extends slightly beyond, an ear canal end of the eartip.

16. A hearing testing probe apparatus comprising:
  a probe tube comprising an outer tube wall extending from an open proximal end to an open distal end, the outer tube wall enclosed between the open proximal end and the open distal end, wherein the outer tube wall comprises a constant outer diameter, the probe tube detachably coupled at the open proximal end to a probe body and extending through a center hole in an eartip to align the open distal end proximate a face of the eartip, wherein the probe tube comprises a rigidity such that a shape of the probe tube is maintained when inserted in the eartip, the probe tube comprising:
  a plurality of stimulus lumens extending within the outer tube wall from the open proximal end to the open distal end of the probe tube, the plurality of stimulus lumens operable to receive a stimulus from at least one receiver at the open proximal end and to carry the stimulus from the open proximal end of the probe tube for output at the open distal end of the probe tube, and
  at least one microphone lumen extending within the outer tube wall from the open proximal end to the open distal end of the probe tube, the at least one microphone lumen operable to receive at least one measured response at the open distal end and to carry the at least one measured response from the open distal end of the probe tube to at least one microphone at the open proximal end of the probe tube.

17. The apparatus of claim 16, wherein the probe tube is operably attached to the hearing testing probe irrespective of the orientation about a longitudinal axis of the probe tube.

18. The apparatus of claim 16, wherein the probe tube is fixably attached to the eartip to form a single entity, wherein the single entity is a single-use disposable component.

19. The apparatus of claim 16, wherein the at least one microphone lumen is a central receiving lumen and the plurality of stimulus lumens are located peripherally to the at least one microphone lumen, the at least one microphone lumen operable to form at least one distinct receiving channel for receiving the at least one measured response, and the plurality of stimulus lumens operable to form at least one transmitting channel for transmitting the stimulus.

20. The apparatus of claim 16, wherein the probe tube terminates flush at, or extends slightly beyond, an ear canal end of the eartip.

21. The apparatus of claim 16, wherein the outer tube wall is a uniform thickness.

22. The apparatus of claim 16, wherein the plurality of stimulus lumens and the at least one microphone lumen are arranged symmetrically within the outer tube wall.

* * * * *